United States Patent
Lemmon et al.

(10) Patent No.: US 11,771,582 B2
(45) Date of Patent: *Oct. 3, 2023

(54) ORTHOPEDIC SHOULDER DEVICE

(71) Applicant: DJO, LLC, Carlsbad, CA (US)

(72) Inventors: Damon Romito Lemmon, Encinitas, CA (US); Thomas Howard Myers, Marietta, GA (US); Charles Edward Garten, II, Atlanta, GA (US); Scott Andrew Taylor, Woodstock, GA (US)

(73) Assignee: DJO, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/588,840

(22) Filed: Jan. 31, 2022

(65) Prior Publication Data

US 2022/0226142 A1 Jul. 21, 2022

Related U.S. Application Data

(63) Continuation of application No. 16/578,817, filed on Sep. 23, 2019, now Pat. No. 11,234,855, which is a continuation of application No. 15/084,368, filed on Mar. 29, 2016, now Pat. No. 10,420,670, which is a continuation of application No. PCT/US2014/058455, filed on Sep. 30, 2014.

(60) Provisional application No. 62/056,814, filed on Sep. 29, 2014, provisional application No. 62/045,469, filed on Sep. 3, 2014, provisional application No. 61/885,394, filed on Oct. 1, 2013.

(51) Int. Cl.
*A61F 5/37* (2006.01)
*A61F 5/01* (2006.01)

(52) U.S. Cl.
CPC ............ *A61F 5/3753* (2013.01); *A61F 5/013* (2013.01); *A61F 5/3738* (2013.01)

(58) Field of Classification Search
CPC ...... A61F 5/3753; A61F 5/3738; A61F 5/013; A61F 5/0118; A61F 5/01; A61F 5/0102; A61F 5/37; A61F 5/373; A61F 5/3715
See application file for complete search history.

(56) References Cited

U.S. PATENT DOCUMENTS

| | | | |
|---|---|---|---|
| 5,385,536 A | 1/1995 | Burkhead et al. | |
| 5,538,499 A | 7/1996 | Schwenn et al. | |
| 6,113,562 A * | 9/2000 | Bonutti | A61F 5/013 602/5 |
| 10,420,670 B2 * | 9/2019 | Lemmon | A61F 5/013 |
| 11,234,855 B2 * | 2/2022 | Lemmon | A61F 5/3753 |
| 2012/0101419 A1 * | 4/2012 | Bonutti | A61F 5/05858 602/20 |

FOREIGN PATENT DOCUMENTS

| | | |
|---|---|---|
| WO | 2006097619 A1 | 9/2006 |
| WO | 2015050897 A1 | 4/2015 |

\* cited by examiner

*Primary Examiner* — Tarla R Patel
(74) *Attorney, Agent, or Firm* — Veros Legal Solutions, LLP

(57) ABSTRACT

Disclosed is a shoulder brace for immobilization of the arm and shoulder joint in neutral abduction/adduction. Methods of using the brace and methods of treating shoulder injuries are similarly provided.

20 Claims, 17 Drawing Sheets

ORTHOPEDIC SHOULDER DEVICE

CROSS REFERENCE TO RELATED APPLICATIONS

This application is a continuation of U.S. Application Ser. No. 16/578,817, filed on Sep. 23, 2019, which is a continuation application of U.S. Application Ser. No. 15/084,368, filed on Mar. 29, 2016, now U.S. Pat. No. 10,420,670, which is a continuation application of International Application No. PCT/US2014/058455, filed Sep. 30, 2014, which claims priority to U.S. Provisional Application No. 61/885,394, filed on Oct. 1, 2013. U.S. Provisional Application No. 62/045,469, filed on Sep. 3, 2014 and U.S. Provisional Application No. 62/056,814, filed on Sep. 29, 2014, the entire contents of which is hereby incorporated by reference.

TECHNICAL FIELD

The present disclosure relates generally to orthoses, and more particularly, to a shoulder orthosis for supporting and stabilizing the shoulder following surgery or injury.

BACKGROUND

The shoulder is a relatively complex joint of the body which is capable of rotation within multiple planes when the arm is displaced relative to the torso. Treatment of shoulder injury frequently requires determining a desired optimal treatment position of the shoulder and associated arm, placement of the shoulder and arm in the desired treatment position. Such a recuperative treatment is particularly applicable to soft tissue injuries involving damage to one or more connective shoulder ligaments and furthermore is often the treatment of choice following any number of surgical procedures, such as surgery for recurrent posterior subluxation, rotator cuff surgery, humeral head or shaft fracture correction, and similar.

Support devices for the shoulder, such as orthopedic braces, rigid casts, and slings are commonly used to perform the placement and immobilization. However, there remains a need for shoulder orthoses which provide greater stability, immobilization, and comfort.

BRIEF DESCRIPTION OF THE DRAWINGS

While the appended claims set forth the features of the present techniques with particularity, these techniques, together with their objects and advantages, may be best understood from the following detailed description taken in conjunction with the accompanying drawings of which:

DETAILED DESCRIPTION OF EXEMPLARY EMBODIMENTS

Figure 1A:
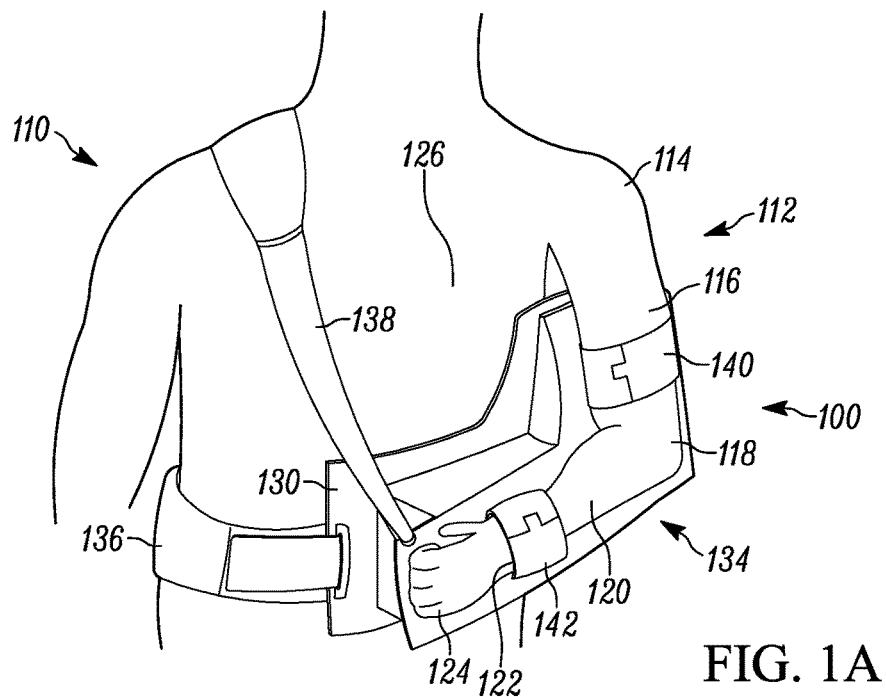
FIG. 1A illustrates a front elevation view of a shoulder brace, or recovery brace, according to an embodiment of the disclosure.

Turning to the drawings, wherein like reference numerals refer to like elements, techniques of the present disclosure are illustrated as being implemented in a suitable environment. The following description is based on embodiments of the claims and should not be taken as limiting the claims with regard to alternative embodiments that are not explicitly described herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The word "othosis" or "orthotic" is used herein to mean a brace or other such device. Consequently, othosis may be used interchangeably with the term "brace" and may refer to specific types of braces when indicated (e.g., a shoulder orthosis or shoulder brace).

The word "neutral" is used herein to mean at or about zero degrees from a centermost position or plane. Thus, when positioning the arm from a user's body, neutral may refer to a plane parallel to a user's spine. In contrast, "resting" is used herein to take into account some deviation from neutral. Thus, when positioning the arm from a user's body, resting may refer to the position the arm naturally rests against the user's body.

Embodiments of this disclosure relate to a shoulder brace for immobilization of the shoulder. Advantages of the shoulder brace include its lightweight construct, easy application, including reduced number of steps to apply brace as well as quick connect fasteners, quick and easy adjustable abduction, and adjustable external/internal rotation. Additional features include the ability to employ a precise amount of abduction and external/internal rotation as well as a breathable design with a drop-out feature.

In some embodiments, a rigid shoulder brace, is provided which immobilizes the arm, and in turn the shoulder joint, in neutral abduction/adduction to 45°, external rotation of between about 0-50° and internal rotation of between about 0-60°. The shoulder orthosis includes a cradle device (e.g., arm shell), an abduction positioning device (e.g., abduction wedge or adduction arch), and a support device (e.g., waist straps or belt). Such orthosis provides a low profile design while minimizing the need for additional straps. Additionally, the cradle device can include a drop out design to allow for flexion/extension of the forearm which facilitates daily living activities.

Current products on the market are bulky and employ a shoulder strap which can impinge on the nerves in the area of the clavicle causing neck pain and discomfort. By using a waist belt design to support the weight of the arm, shoulder devices or orthosis provided herein eliminate the need for shoulder straps, thus eliminating the associated pain and discomfort. Additionally the low profile design of the waist belt and abduction positioning device reduce the bulk and weight seen in other designs and allow for more breathability, thus reducing patient discomfort while wearing the orthosis.

In some embodiments, multiple pathologies can be addresses with one orthosis, including, but not limited to: glenohumeral dislocation or subluxation, capsular shifts, posterior shoulder stabilizations, Bankart repairs, release severe anterior capsule contracture, soft tissue strains or repairs, rotator cuff repairs, total shoulder replacement, superior labral repairs (SLAP), shoulder debridment, fractures (humerus, elbow, forearm), biceps tendon repair, elbow ligament/tendon repair, anterior shoulder lauxation and AC joint reconstruction.

Referring to FIG. 1A, a front elevation view illustrates a shoulder brace 100 according to one embodiment of the disclosure, in a fully-assembled state as worn by a user 110. Shoulder brace 100 may be designed to facilitate the recovery of the user 110. The user 110 may have an arm 112 connected to the body of the user 110 with a shoulder 114.

The arm 112 may include an upper arm 116, an elbow 118, a forearm 120, a wrist 122, and a hand 124. The user may further have a torso 126.

The brace 100 may be designed to help the user 110 to recover from a surgical procedure such as described above, which may necessitate a variety of arm positions for recovery. Known recovery braces such as slings and other shoulder immobilizers, in many cases, lack the flexibility to be used to facilitate recovery from different types of injury or surgery. The user 110 would benefit from a device that allows stable positioning of the shoulder at different angles to facilitate recovery from a wide variety of shoulder procedures.

Brace 100 may have a modular design that facilitates the positioning of the arm 112 at multiple different orientations relative to the torso 126 of the user 110. More particularly, the brace 100 may have a body member 130, a spacer 132, an arm member 134, a waist strap 136, and a shoulder strap 138. The body member 130 may rest against the torso 126 of the user 110, and may be held in place by the waist strap 136. The waist strap 136 may be formed of a flexible material, and may have an adjustable length, or may be adjustably secured to the body member 130 via buckles, clasps, fasteners such as a hook and loop fastener, or the like.

The arm member 134 may be attached to and spaced apart from the body member 130 via the spacer 132, which may have a wedge shape that positions the forearm 120 further from the torso 126 than the upper arm 116, allowing for a relatively natural position of the arm 112. The shoulder strap 138 may be used to support the body member 130 and/or the arm member 134 at the desired elevation, with the aid of the other shoulder of the user 110.

The arm member 134 may have an upper arm band 140 and a wrist band 142 that grip the upper arm 116 and the wrist 122 of the user 110, respectively. The upper arm band 140 and the wrist band 142 may each include a flexible strap or other element that is detachably secured to the arm 112. Buckles, clasps, fasteners such as hook and loop fasteners, or other detachable elements may be used. Optionally, a forearm band (not shown) may be included, which may grip the forearm 120 of the user 110. Such a forearm band, if included, may be located between the wrist band 142 and the elbow 118 of the user 110.

Advantageously, the independent attachment of the brace 100 to the arm 112 may enable the user 110 to carry out certain tasks that may not be possible with known brace designs. For example, the wrist band 142 may be detached from the wrist 122 to enable the user 110 to perform functions that may require two hands, such as eating, washing, typing, driving or the like. Once the activity is complete, the wrist band 142 may be re-attached to the wrist 122 to again provide support to the wrist 122.

Figure 1B:
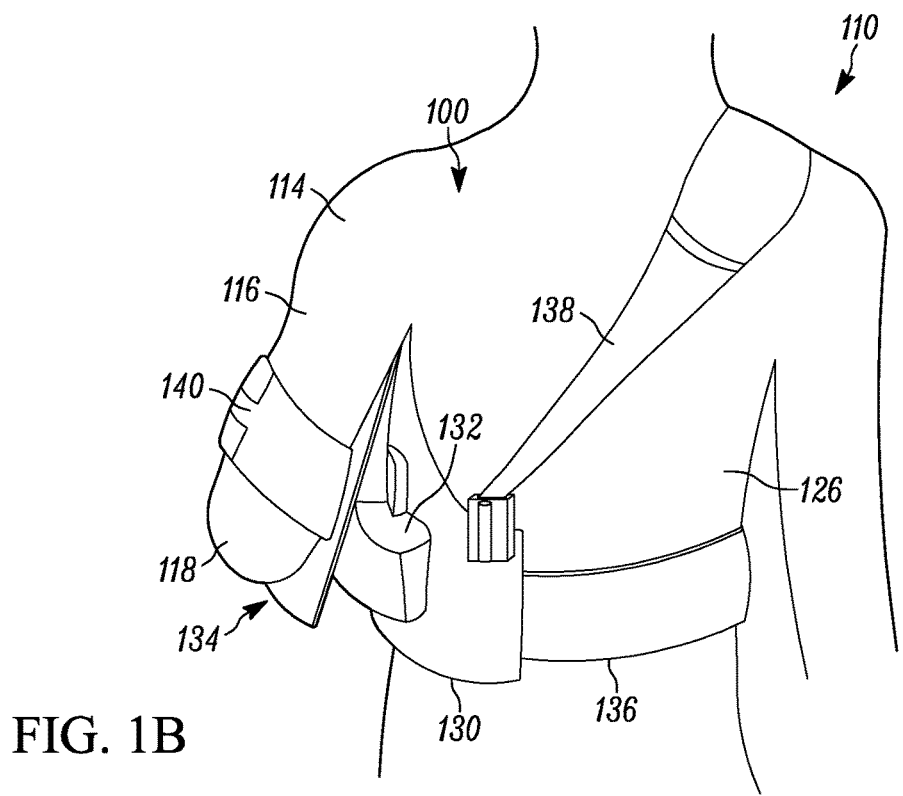
FIG. 1B illustrates a rear elevation view of the shoulder brace of FIG. 1A, in a fully-assembled state as worn by a user.

Referring to FIG. 1B, a rear elevation view illustrates the brace 100 of FIG. 1A, in a fully-assembled state as worn by the user 110. As further shown in FIG. 1B, the shoulder strap 138 may be secured to the body member 130 on the rear, and to the arm member 134 on the front. In alternative embodiments, the front and back ends of the shoulder strap 138 may be secured to any combination of the body member 130, the spacer 132, the arm member 134, the waist strap 136, and/or any other acceptable anchor point, including other straps or items of apparel worn by the user 110.

Figure 2A:
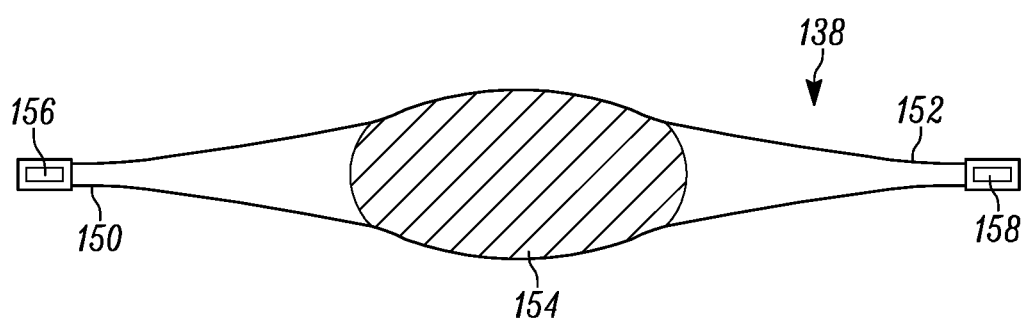
FIG. 2A illustrates a plan view of a shoulder strap of the shoulder brace of FIGS. 1A and 1B.

Referring to FIG. 2A, a plan view illustrates the shoulder strap 138 of the brace 100 of FIGS. 1A and 1B in greater detail. As shown, the shoulder strap 138 may have a forward end 150, a rearward end 152, and an intermediate portion 154. The forward end 150 may be detachably connected to the arm member 134 as shown in FIG. 1A. The forward end 150 may have a forward fastener 156, which may be a buckle that engages a corresponding member permanently attached to the arm member 134. Similarly, the rearward end 152 may be detachably connected to the body member 130 as shown in FIG. 1B. The rearward end 152 may have a rearward fastener 158, which may also be a buckle that engages a corresponding member permanently attached to the body member 130.

In some embodiments, the forward fastener 156 and/or the rearward fastener 158 may include other fastening elements besides buckles. Such fastening elements include, but are not limited to clips, clasps, hook and loop systems, and the like.

If desired, the intermediate portion 154 may be wider than the forward end 150 and/or the rearward end 152, as illustrated, in order to distribute the weight carried by the shoulder strap 138 over a broader portion of the other shoulder of the user 110. Additionally or alternatively, the intermediate portion 154 may include padding, more and/or less abrasive materials, and/or other aspects that enhance the comfort level of the user 110, who may be wearing the brace 100 for an extended period of time.

Figure 2B:
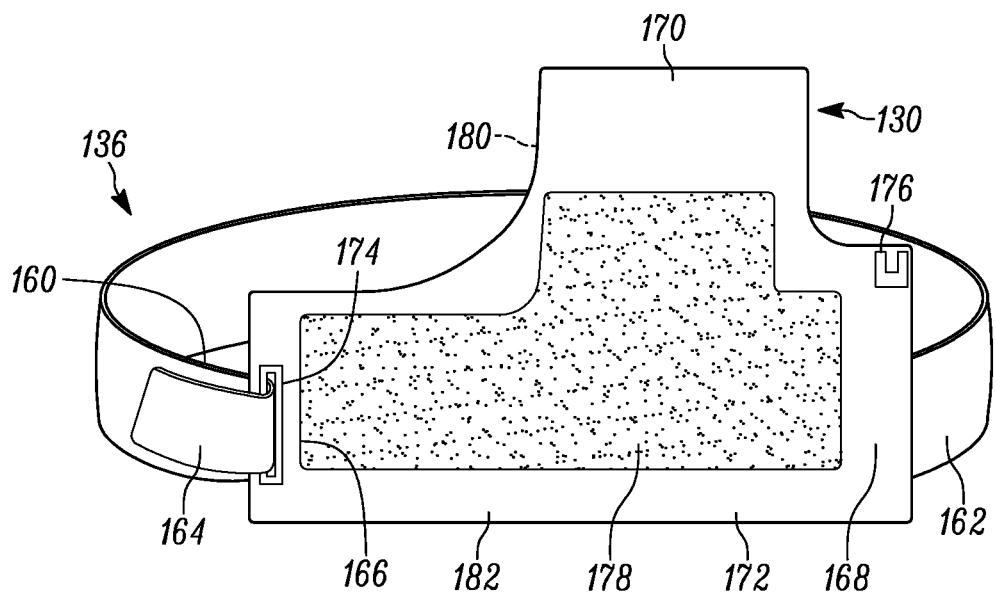
FIG. 2B illustrates a side elevation view of a body member and a waist strap of the shoulder brace of FIGS. 1A and 1B.

Referring to FIG. 2B, a side elevation view illustrates the body member 130 and the waist strap 136 of the brace 100 in isolation from the remaining components of the brace 100. As shown, the waist strap 136 may have a first end 160 and a second end 162. The first end 160 may be secured to the body member 130 through the use of a first fastener 164, which may be adjustable to allow the recovery brace 100 to be used for patients of different sizes, genders, ages, etc. The first fastener 164 may optionally include a hook and loop fastener that can easily be fastened at multiple different positions to effectively vary the length of the waist strap 136. The second end 162 may be attached to the body member 130 via a similar fastening arrangement, with a different removable fastening system, or via a permanent attachment whereby the length of the waist strap 136 is adjusted only via the first fastener 164.

The body member 130 may have a forward end 166, a rearward end 168, a top end 170, and a central portion 172. The body member 130 may optionally have a T-shape as shown, wherein the forward end 166, the rearward end 168, and the top end 170 each define extensions from the central portion 172. The T-shape illustrated may provide for enhanced user comfort via the forward end 166 and the rearward end 168, while enhancing the support provided to the arm 112 via the top end 170. However, the T-shape shown in FIG. 2B is optional, and may be replaced with a wide variety of shapes.

The body member 130 may be attached to the waist strap 136 as shown, and also to the spacer 132 and the shoulder strap 138, as shown in FIGS. 1A and 1B. Thus, the body member 130 may have a plurality of attachment features that facilitate such attachment.

For example, the body member 130 may have a forward attachment feature 174 that facilitates attachment of the first fastener 164 of the waist strap 136 to the body member 130. As shown, the forward attachment feature may simply be a slot through which the first end 160 of the waist strap 136 passes. The body member 130 may also have a rearward attachment feature (not shown) that attaches to the second end 162 of the waist strap 136, either detachably or permanently as set forth above.

Additionally, the body member 130 may have a shoulder strap fastener 176 that is attachable to the rearward end 152 of the shoulder strap 138. The shoulder strap fastener 176 may include a buckle, receiver, or other fastening element that is easily coupled to the rearward fastener 158 of the shoulder strap 138. The shoulder strap fastener 176 may be positioned on or near the rearward end 168 of the body member 130 as shown.

Yet further, the body member 130 may have a spacer fastener 178 positioned on the central portion 172 of the body member 130. The spacer fastener 178 may be designed to removably attach the spacer 132 to the body member 130. In the embodiment shown in FIG. 2B, the spacer fastener 178 may include a component of a hook and loop fastening system (such as an array of loops) that mates with a corresponding component on the surface of the spacer 132 that faces the body member 130. The spacer fastener 178 may cover a relatively wide area on the body member 130 so as to provide secure attachment of the spacer 132 to the body member 130.

The body member 130 may be formed of one or more sturdy, rigid, lightweight materials. The body member 130 may beneficially be formed of water-resistant materials so that the brace 100 can be used in a shower, bath, swimming pool, or other aqueous environment. The spacer 132, the arm member 134, the waist strap 136, and the shoulder strap 138 may similarly be formed of water-resistant materials.

If desired, the body member 130 may be curved or otherwise contoured to lie against the torso 126 of the user 110. More precisely, an inward-facing surface 180 (the surface of the body member 130 that faces the torso 126, which faces away from the viewpoint of FIG. 2B) may be curved about a vertical axis such that the forward end 166 and the rearward end 168 of the body member 130 both curve toward the waist strap 136. Additionally or alternatively, the body member 130 may be curved about a horizontal axis such that the top end 170 is angled inward or outward, toward or away from the torso 126. The body member 130 may have an outward-facing surface 182 with similar contouring, or the outward-facing surface 182 may be substantially planar so as to promote secure attachment of the spacer fastener 178 with the spacer 132. If the inward-facing surface 180 is curved, the outward-facing surface 182 may be made planar by varying the thickness of the body member 130, for example, by making the body member 130 thicker at the forward end 166 and/or the rearward end 168, where the inward-facing surface 180 is curved toward the waist strap 136.

Contouring of the body member 130 may optionally be customized to the patient. For example, the brace 100 may be one of a kit including several body members 130 that differ from each other in size, curvature, and/or other characteristics. The body member 130 to be used for the user 110 may be selected from the kit based on the size, shape, gender, surgery type, and/or other characteristics of the user 110.

Additionally or alternatively, contouring of the body member 130 may be customized by molding, bending, or otherwise shaping the body member 130 to fit the body of the brace 100. For example, the body member 130 may include a thin metal core (not shown), which may be sheathed in a fabric, mesh, polymer, or other softer cover. The metal core may be bendable, by hand, or through the use of a mechanical bender, to fit the brace 100. A core made of a plastics, ceramic, composite, or other material may additionally or alternatively be used. A shape memory alloy or other thermally active material may be used to enable the application of thermal energy to the metal core to facilitate shaping of the body member 130 and/or cause the body member 130 to retain the shape applied.

Furthermore, the inward-facing surface 180 of the body member 130 may have a corrugated, mesh-like, or otherwise irregular surface. Such surface irregularity may help avoid sweating or chafing of the user 110 by facilitating air exchange with the surface of the torso 126 in contact with the body member 130.

Figure 3:
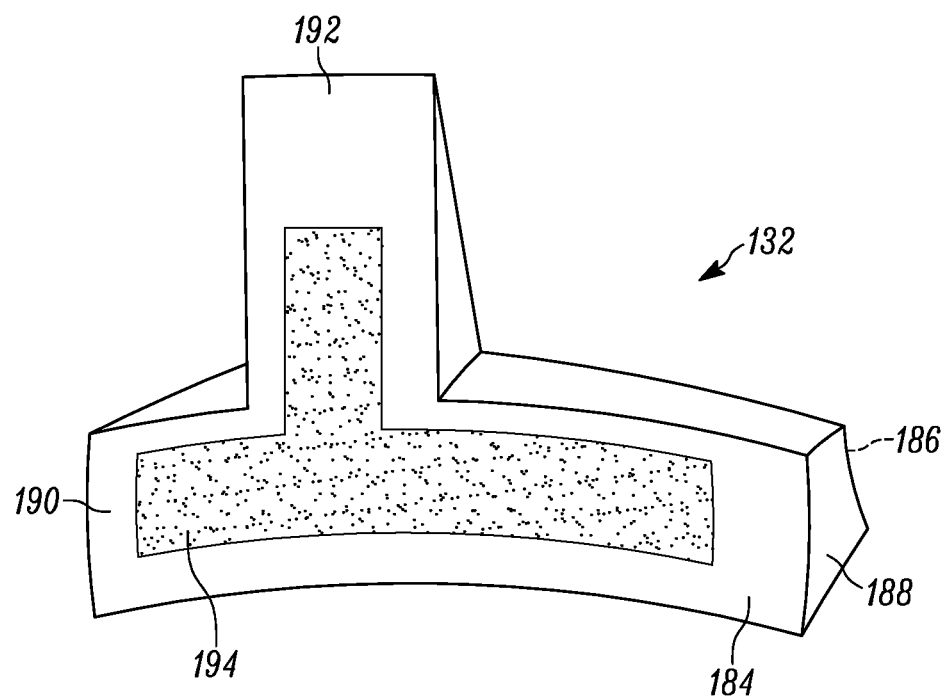
FIG. 3 illustrates a perspective view of a spacer of the shoulder brace of FIGS. 1A and 1B.

Referring to FIG. 3, a perspective view illustrates the spacer 132 of the brace 100 of FIGS. 1A and 1B in greater detail. As shown, the spacer 132 may have an inward-facing surface 184 that attaches to the outward-facing surface 182 of the body member 130, and an outward-facing surface 186 that attaches to the inward facing surface of the arm member 134. Further, the spacer 132 may have a forward end 188, a rearward end 190, and a top end 192, which may, after attachment of the spacer 132 to the body member 130, lie alongside the forward end 166, the rearward end 168, and the top end 170 of the body member 130, respectively. The spacer 132 may thus have a T-shape that generally conforms to the shape of the body member 130.

The spacer 132 may have a body member fastener 194 that is designed to be removably attached to the spacer fastener 178 of the body member 130. The body member fastener 194 may thus be of a type complementary to that of the spacer fastener 178. For example, if the spacer fastener 178 is the loop component of a hook and loop fastening system, the body member fastener 194 may be the hook component that interfaces with and attaches to it. The body member fastener 194 may cover a large portion of the surface 184 so as to provide secure attachment of the spacer 132 to the body member 130.

The spacer 132 may have a wedge shape as shown in FIG. 3. More precisely, the spacer 132 may be angled such that the bottom is thicker than the top, thus positioning the surface 186 and the surface 184 at a nonzero angle relative to each other. As shown, this angle may be 15°. However, in alternative embodiments, a larger or smaller angle may be used. For example, the angle may range from 0° to 30°. Further, the angle may range from 5° to 25°. Yet further, the angle may range from 10° to 20°. The angle between the inward-facing surface 184 and the outward-facing surface 186 may not be uniform if either of the inward-facing surface 184 and the outward-facing surface 186 is non-planar.

The inward-facing surface 184 may have a shape that matches that of the outward-facing surface 182 of the body member 130. Thus, if the outward-facing surface 182 of the body member 130 is planar, the inward-facing surface 184 may also be planar. Similarly, if the outward-facing surface 182 of the body member 130 is contoured, the inward-facing surface 184 may have a matching contour. The outward-facing surface 186 may similarly have a shape that matches that of the arm member 134, and may thus be planar or contoured as well. The inward-facing surface 184 and the outward-facing surface 186 may have the same or different planarity or contouring. Thus, the spacer 132 may have a uniform thickness or a variable thickness from the forward end 188 to the rearward end 190. The spacer 132 may be formed of a relatively rigid, lightweight substance such as rigid foam.

The wedge shape of the spacer 132 may help to angle the arm 112 of the user 110 so that the elbow 118 is positioned some distance from the torso 126. This displacement may help to position the shoulder 114 of the user 110 in a position that more properly facilitates recovery of the shoulder 114, depending on the procedure from which recovery is needed. If desired, the brace 100 may be positioned to enable the arm 112 to be positioned at a variety of angles and displacements relative to the body member 130. For example, a kit according to the disclosure may include a plurality of spacers 132 of different shapes and sizes. In such a kit, the spacers 132 may have a variety of angles between the inward-facing surface 184 and the outward-facing surface 186 so that the arm 112 of the user 110 can be positioned at the appropriate position.

Additionally or alternatively, a spacer 132 may be custom-shaped to suit the user 110. The spacer 132 may be cut to the appropriate size prior to attachment to the body member 130 and/or the spacer 132. Alternatively, the spacer 132 may be formed of a shape memory substance such as rigid memory foam. The spacer 132 may be compressed, molded, or otherwise formed into the desired shape, and then the appropriate activation mechanism (such as temperature) may be used to keep the spacer 132 in that shape.

In alternative embodiments, a spacer (not shown) may have an adjustable shape. For example, such a spacer may be shaped like the spacer 132 of FIG. 3, but with an inward-facing surface and an outward-facing surface that are on separate members that are translatably and/or pivotably coupled together with a hinge, worm gear, lockable sliding interface, or the like to enable the angle and/or spacing between the inward-facing surface and an outward-facing surface to be adjusted. Such a design may obviate the need for a kit with multiple spacers.

Figure 4:
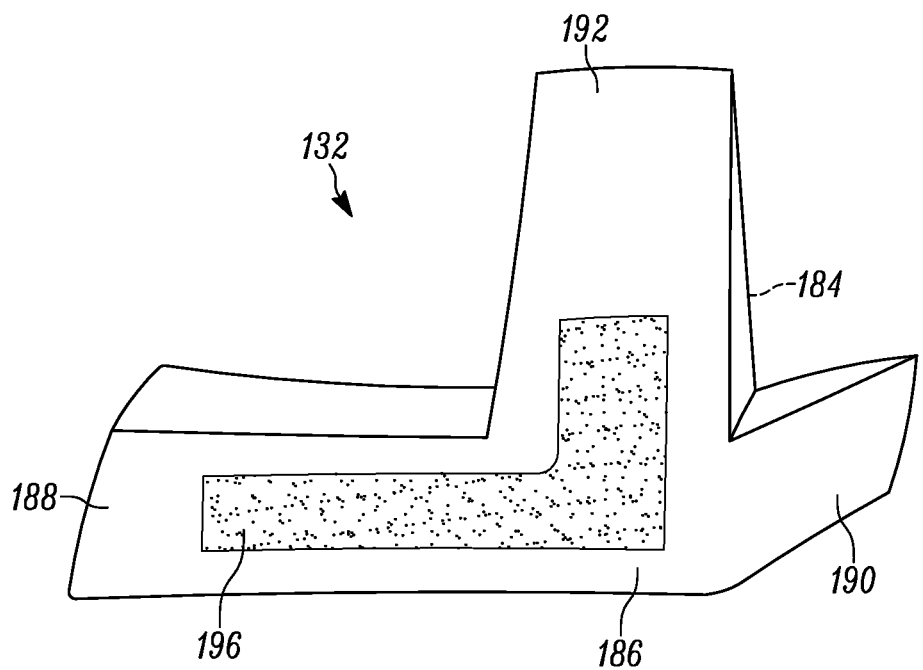
FIG. 4 illustrates a perspective view of the spacer from a viewpoint generally opposite to that of FIG. 3.

Referring to FIG. 4, a perspective view illustrates the spacer 132 of the brace 100 of FIGS. 1A and 1B from a viewpoint generally opposite to that of FIG. 3. FIG. 4 more clearly illustrates one possible shape of the spacer 132 in which the surface 184 may be contoured while the surface 186 is substantially planar.

As shown, an arm member fastener 196 may be attached to the outward-facing surface 186 to attach the arm member 134 to the spacer 132. Like the spacer fastener 178 and the body member fastener 194, the arm member fastener 196 may be any type of fastening device. As shown in FIG. 4, the arm member fastener 196 may be a component of a hook and loop fastening system, and may more specifically be the hook component.

Figure 5A:
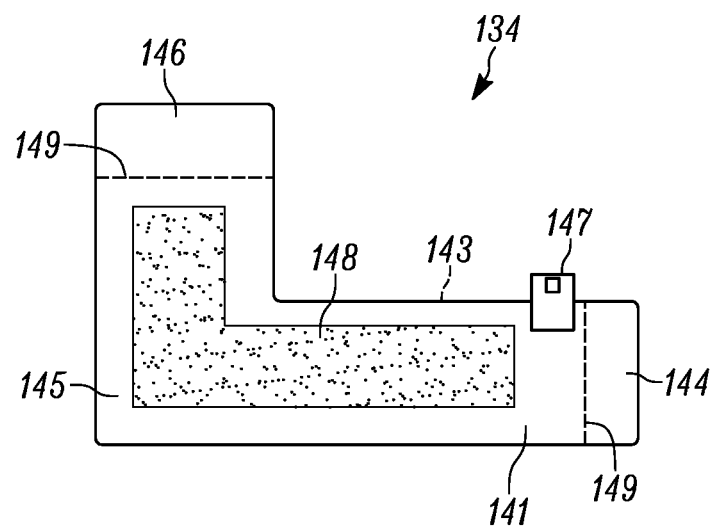
FIG. 5A illustrates a rear elevation view of an arm member of the shoulder brace of FIGS. 1A and 1B.

Referring to FIG. 5A, a rear elevation view illustrates the arm member 134 in greater detail. As shown, the arm member 134 may have an inward-facing surface 141 and an outward-facing surface 143. The arm member 134 may further have a forward end 144, a rearward end 145, and a top end 146, which may generally align with the forward end 166, the central portion (forward of the rearward end 168), and/or the top end 170, respectively, of the spacer 132.

The arm member 134 may have an L-shape that generally parallels that of the arm 112 of the user 110. The arm member 134 may be formed of a relatively stiff, durable material such as high-density foam. A fabric covering or the like may optionally be used. The arm member 134 may be substantially flat as shown. Alternatively, the arm member 134 may have contouring to enable it to more closely match the shape of the arm 112.

The arm member 134 may have a shoulder strap fastener 147, which may be similar to the shoulder strap fastener 176 of the body member 130. The shoulder strap fastener 147 may thus include a buckle, receiver, or other fastening element that is easily coupled to the forward fastener 156 of the shoulder strap 138. The shoulder strap fastener 147 may be positioned on or near the forward end 144 of the arm member 134 as shown.

The arm member 134 may also have a spacer fastener 148 that facilitates attachment of the arm member 134 to the spacer 132. The spacer fastener 148 may be designed to be removably attached to the arm member fastener 196 of the spacer 132. The spacer fastener 148 may thus be of a type complementary to that of the arm member fastener 196. For example, if the arm member fastener 196 is the hook component of a hook and loop fastening system, the spacer fastener 148 may be the loop component that interfaces with and attaches to it. The spacer fastener 148 may cover a large portion of the inward-facing surface 141 so as to provide secure attachment of the arm member 134 to the spacer 132.

The arm member 134 may also be part of a kit with multiple arm members 134 of different shapes and/or sizes to enable the brace 100 to be used for patients of different sizes, shapes, and genders. Thus, an arm member 134 of the proper size and/or shape may simply be selected from those within the kit.

Alternatively, the arm member 134 may be modifiable to customize it for a given patient. For example, like the body member 130, the arm member 134 may optionally be include a thin metal plate, shape memory material, or other structure malleable enough to permit the arm member 134 to be shaped to fit the arm 112 of the user 110.

Additionally or alternatively, the arm member 134 may be large enough for larger patients, and may be cut down to size for smaller patients. For example, the arm member 134 may have break lines 149 positioned proximate the forward end 144 and the top end 146. The break lines may be locations at which the arm member 134 may be relatively easily broken to shorten the forward end 144 and/or the top end 146. The arm member 134 may thus have a thin section, pre-stressed region, crack, or other feature at the break lines that makes the break lines 149 relatively natural locations that promote clean, distinct breaks for shortening of the forward end 144 and/or the top end 146.

Figure 5B:
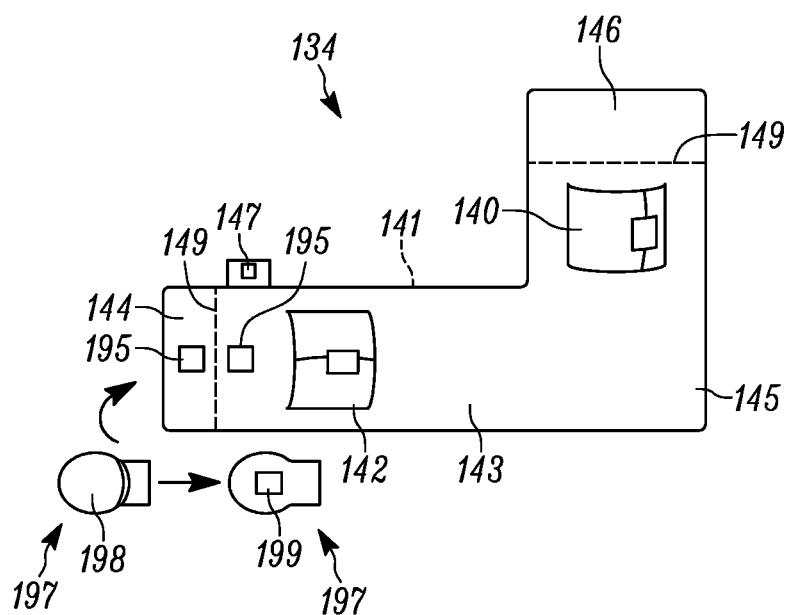
FIG. 5B illustrates a front elevation view of the arm member of the shoulder brace of FIGS. 1A and 1B.

Referring to FIG. 5B, a front elevation view illustrates the arm member 134 of the brace 100 of FIGS. 1A and 1B from a viewpoint nearly opposite to that of FIG. 5A. As shown, the upper arm band 140 and the wrist band 142 may have fabric or polymer bands or other elements that wrap around the upper arm 116 and the wrist 122, respectively, of the user 110. The upper arm band 140 and the wrist band 142 may each include a fastener such as a buckle, clasp, hook and loop fastening system, or the like that permits relatively rapid and easy attachment to and detachment from the arm 112 of the user 110.

The arm member 134 may also have a grip 197 proximate the forward end 144. The grip 197 may have a rounded shape that provides a resting place for the hand of the user 110. The arm member 134 may have two grip fasteners 195, either of which may receive the grip 197 to secure the grip 197 to the outward-facing surface 143. Each of the grip fasteners 195 may constitute any known fastener type. If desired, each of the grip fasteners 195 may be a component of a hook and loop fastening system or the like, such as the loop component illustrated in FIG. 5B.

Each of the grips 197 may have a grip portion 198 and an arm member fastener 199 positioned on an opposite side of the grip 197 from the grip portion 198. The grip portion 198 may have an ergonomic shape suitable for the user to rest his or her hand on the grip portion 198. Accordingly, the grip portion 198 may have a semispherical shape, an ovoid shape, or the like. The grip portion 198 may be rigid, or may have a soft and/or textured surface. If desired, the grip portion 198 may have a flexible shell filled with a gel or other substance designed to be comfortable to the hand of the user 110.

In alternative embodiments, a grip portion (now shown) may have an interface that receives users input so that a user can perform activities while wearing the recovery brace. For example, such a grip portion may include an integrated computer mouse, computer keyboard, vehicular driving controls, remote control, smartphone holder, and/or a variety of other items that can receive user input without requiring the user to detach any part of the brace 100 from his or her arm.

The arm member fastener 199 may be of a type complementary to the grip fasteners 195. Thus, if the grip fasteners 195 are the loop components of hook and loop fastening systems, the arm member fastener 199 may be the hook portion of such a hook and loop fastening system. The arm member fastener 199 may thus be attached to either of the grip fasteners 195 to attach the grip 197 to the desired location on the outward-facing surface 143.

As shown, the grip fasteners 195 may be positioned on either side of the break line 149 that is positioned at the forward end 144. Thus, for a patient with a longer arm, the grip 197 may be secured to the grip fastener 195 that lies forward of the break line 149. For a patient with a shorter arm, the forward end 144 may be severed at the break line 149 and the grip 197 may be secured to the remaining grip fastener 195, e.g., the grip fastener 195 that lies rearward of the break line 149.

Figure 6:
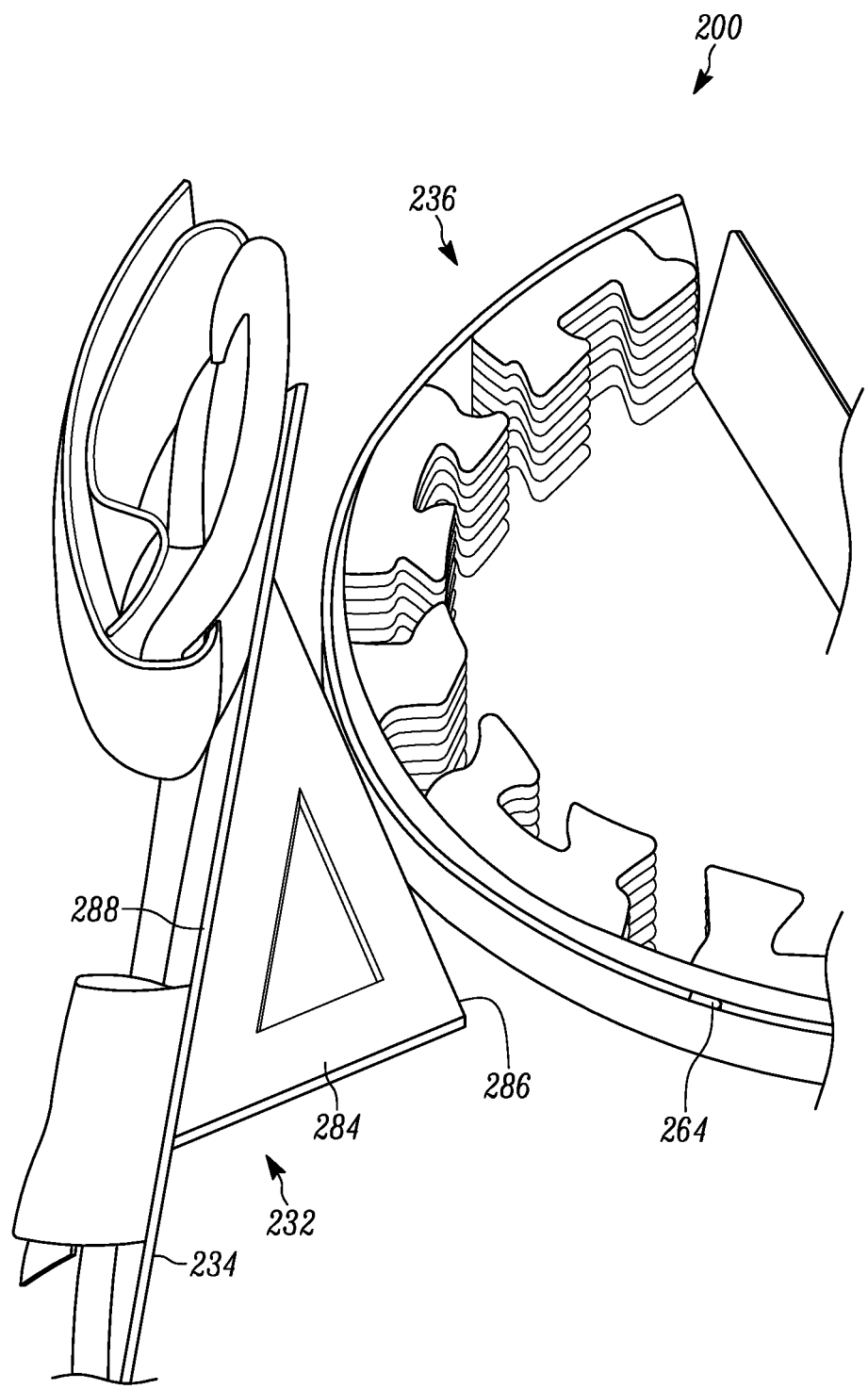
FIG. 6 illustrates a perspective view of a shoulder brace according to an embodiment of the disclosure.

Referring to FIG. 6, a perspective view illustrates a shoulder brace 200 according to an embodiment of the disclosure. As shown, the brace 200 may have a body member 230, a spacer 232, an arm member 234, a waist strap 236, and a shoulder strap (not shown) that may be similar to their counterparts of the brace 100. Some of the features of the brace 200 that differ from those of the brace 100 will be described below.

The body member 230 may generally have a flexible configuration, which may allow it to fit instantly to the shape of the torso 126 of the user. The body member 230 may have an inward-facing surface 280 that has a corrugated shape. The corrugated shape of the inward-facing surface 280 may serve a number of functions. For example, the corrugated shape may facilitate bending of the inward-facing surface 280 to match the shape of the torso 126 of the user 110. Further, the corrugated shape may permit airflow adjacent to the skin and/or clothing covering the torso 126 to help prevent excessive sweat, chafing, skin irritation, and other problems that may occur with insufficient airflow to a person's skin. The corrugation illustrated is merely exemplary; in other embodiments, an inward-facing surface may have corrugations that are smaller, larger, differently-oriented, and/or differently-shaped. Alternatively, an inward-facing surface may have a mesh shape or other shape that provides for airflow against the torso 126 and/or clothing, without having a pattern of ridges and/or grooves.

The waist strap 236 may also be different from the waist strap 136. For example, rather than attaching to forward and rearward ends of the body member 230, the waist strap 236 may encircle the body member 230 and the torso 126, with ends that fasten together at a fastener 264. The fastener 264 may be a buckle, clip, or other feature that secures the ends of the waist strap 236 together. If desired, the body member 230 may have loops or other features that engage the waist strap 236 to ensure that the waist strap 236 remains properly positioned on the body member 230 as the brace 200 is used.

The spacer 232 may also be different from the spacer 132. For example, the spacer 232 may have a triangular shape or wedge shape that is designed to permit the spacer 232 to be used to secure the arm member 234 to the body member 230 in multiple relative orientations. The spacer 232 may, for example, have the shape of a right triangle as shown in FIG.

6. The spacer 232 may thus have a first side 284, a second side 286, and a third side 288.

The angle between the first side 284 and the second side 286 may be 90°, give or take 5°, 10°, 15°, 20°, or 25°. The angle between the second side 286 and the third side 288 may be 30°, give or take 5°, 10°, 15°, 20°, or 25°. The angle between the first side 284 and the third side 288 may be 60°, give or take 5°, 10°, 15°, 20°, or 25°. The angles between the first side 284, the second side 286, and the third side 288 may cause the length of the second side 286 to be less than that of the third side 288, but more than that of the first side 284.

The body member 230 and the arm member 234 may be attached to any combination of the first side 284, the second side 286, and the third side 288. The sides of the spacer 232 to which the body member 230 and the arm member 234 are attached may be selected based on the angle at which the arm 112 is to extend relative to the torso 126. For example, where the wrist 122 of the arm 112 is to be held relatively close to the torso 126, the body member 230 and the arm member 234 may be attached to the second side 286 and the third side 288, as shown, so that the angle between the body member 230 and the arm member 234 is relatively small.

By changing how the body member 230 and arm member 234 are attached (e.g., by changing the location that arm member 234 is attached to spaces 232, the brace 200 may be configured, as in FIG. 6, to keep the wrist 122 relatively close to the torso 126. However it is appreciated that the arm 112 may be supported by the brace 200 in other positions relatively close to the torso 126 of the user 110. For example, the body member 230 may be attached to the second side 286 of the spacer 232 and the arm member 234 may be attached to the third side 288 of the spacer 232.

In other embodiments, brace 200 can extend the wrist 122 of the arm 112 relatively further from the torso 126. For example, attaching to the third side 288 of the spacer 232, and the arm member 234 may be attached to the first side 284 of the spacer 232. This may cause the angle between the body member 230 and the arm member 234 to correspond to the angle between the third side 288 and the first side 284 (for example, 60°), rather than the smaller angle between the second side 286 and the third side 288 (for example, 30°).

Additionally, the spacer 232 may be attachable to the body member 230 and/or the arm member 234 at multiple locations. These locations may further permit adjustment of the angle and/or position of the arm 112 relative to the torso 126. In particular, the flexibility of the body member 230 may provide it with a rounded shape when worn by the user 110; the location of the spacer 232 on the body member 230 may help determine the angle at which the arm 112 is disposed relative to the torso 126. Other configurations may also be obtained through the repositioning and/or reorientation of the various parts of the brace 200.

Figure 7:
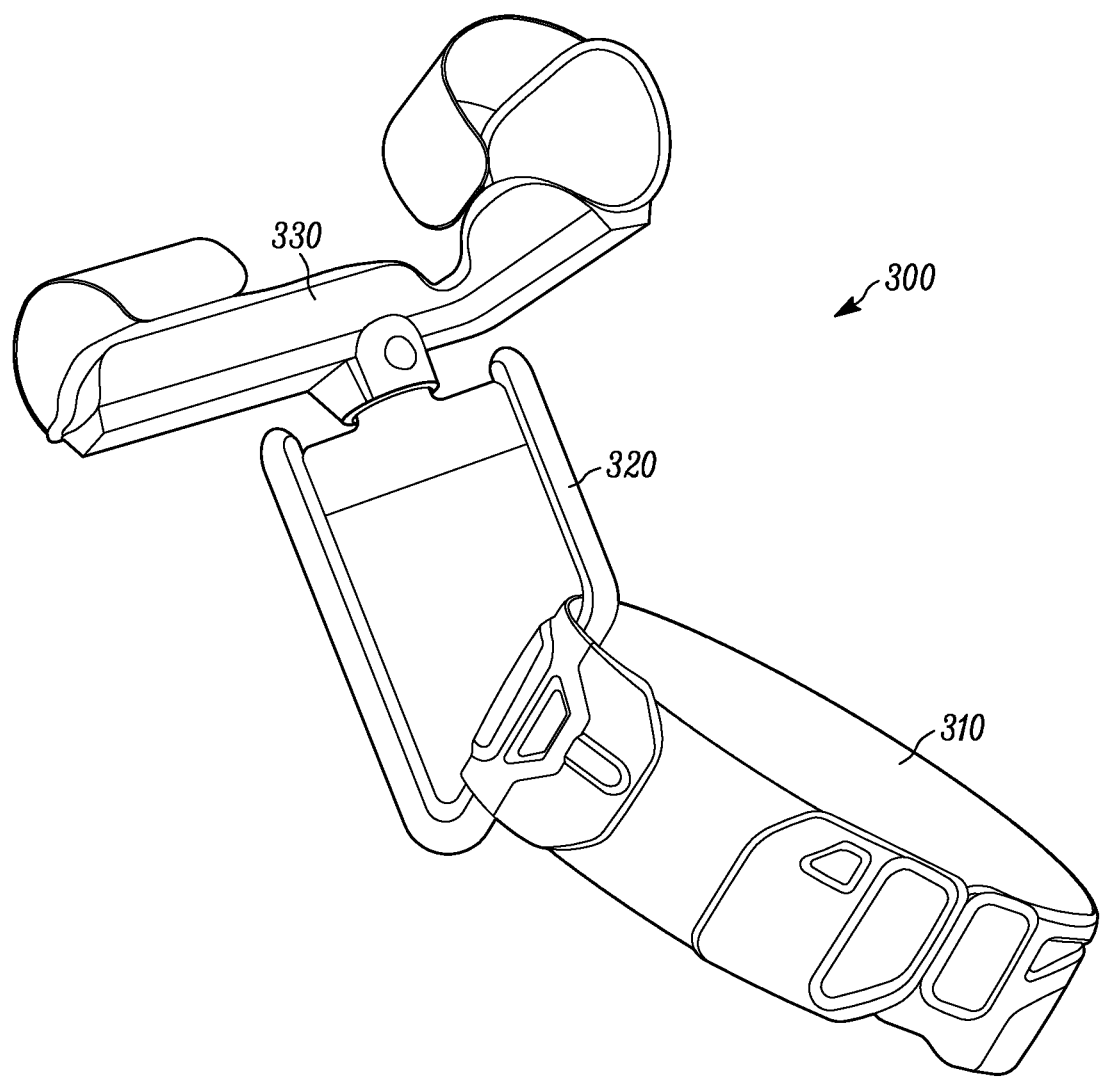
FIG. 7 illustrates a shoulder brace according to an embodiment of the disclosure.

FIG. 7 illustrates a shoulder brace 300 according to an embodiment of the disclosure. Shoulder brace 300 includes three primary components: a support device 310, an abduction positioning device 320 and a cradle device 330. In some embodiments, support device 310 includes a plurality of panels, a soft belt portion and fasteners. In some embodiments, the abduction positioning device 320 includes a rotation coupling member, a wedge frame, and a rotational insert. In some embodiments, the cradle device 330 includes an arm shell and a plurality of fasteners.

Figure 8:
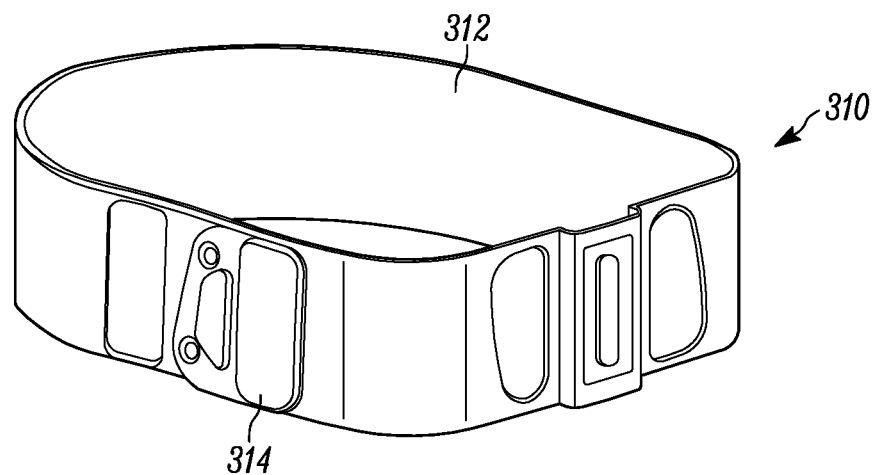
FIG. 8 illustrates a waist belt having a flat orientation prior to fitting the belt to a patient.

FIG. 8 illustrates a support device 310 or waist belt having a flat orientation prior to fitting the belt to a patient. Turning more particularly to the support device 310 of FIG. 8, the support device 310 includes a plurality of panels (such as front outer and inner attachment panels and a center panel, shown collectively as 314) to provide support and rigidity to a fastener (not shown) such as a Fidlock® fastener or any suitable magnetic fastening or buckling interface. The panels 314 themselves may be constructed from a polyethylene or ethylene vinyl acetate (EVA) foam (e.g., low density 70 kg/m3) and are approximately 6 in.×6 in.×0.25 in. In some embodiments, the fasteners are attached to the panels 314 by threading them through holes cut into the panels 314. The panels 314 are, in turn, attached to the soft belt portion 312 via. e.g., a Velcro hook adhered to the backside of the panels 314 using pressure sensitive adhesive.

Figure 9:
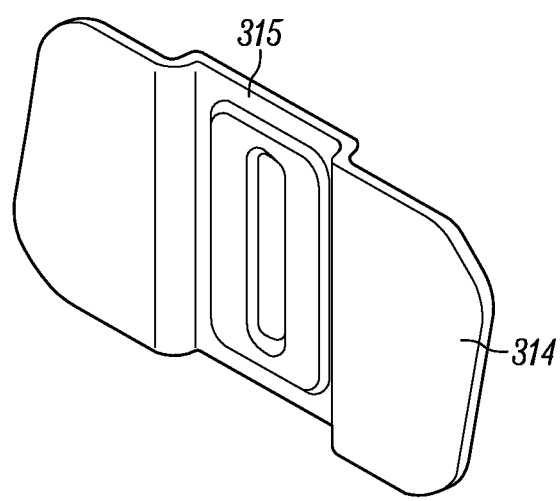
FIG. 9 illustrates a rear isometric view of a waist belt center panel.

A center panel 314 may be configured to provide support and rigidity to the soft belt portion 312 and abduction positioning device 320. The center panel 314 may be constructed from a polyethylene or EVA foam (high density 80 kg/m3) and is approximately 12 in.×6 in.×0.25 in. The center panel 314 may have a contoured geometry such that the abduction positioning device 320 can nest within the center panel 314 and be prevented from rotating relative to the support device 310. The overall height of the center panel 314 with the contour is approximately 0.70 in. The center panel 314 may be attached to the soft belt portion 312 via sewing. In some embodiments, a channel or groove 315 is molded in the center panel 314, and extends the length of the panel 314. See FIG. 9. As shown, the groove 315 may be configured to receive and retain an abduction wedge frame of the abduction positioning device 320.

In some embodiments, the soft belt portion 312 may be constructed from a perforated polyethylene or EVA core with moisture wicking spacer fabric laminated on the inside and a mesh loop fabric laminated on the outside. The soft belt portion 312 may be approximately 36 in.×6 in.×0.25 in. In some embodiments, soft belt portion 312 is configured to be cut to size for an individual patient or user.

In some embodiments, the center panel 314 is sewn to two instances of the soft belt portions 312 on either side of the panel 314. There may be a channel within the center panel 314 along which the stitching will follow to secure the components together. Coming off either end of the soft belt portions 312 are the front outer and inner attachment panels 314. Both of these panels 314 are adhered to the outer mesh loop laminate of the soft belt portions 312 by hook that is adhered to the panels 312 with a pressure sensitive adhesive. On the outer attachment panel 314 two instances of Fidlock® fasteners are attached through two holes cut in the panel. On the inner attachment panel 314 two instances of corresponding Fidlock® fasteners are attached through two holes cut in the panel. When the belt is wrapped around the patient's torso the outer and inner panels can be brought together and are magnetically and mechanically locked.

Figure 10:
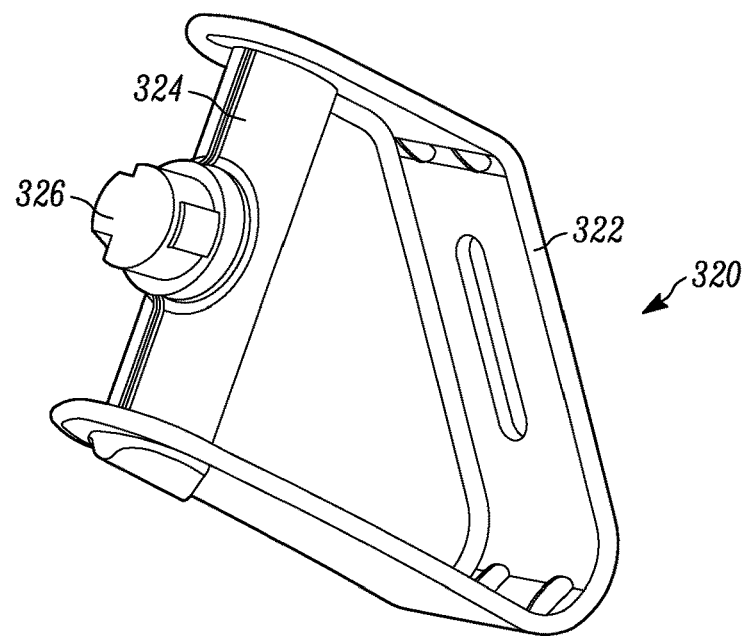
FIG. 10 illustrates an isometric view of a wedge assembly.

FIG. 10 illustrates an isometric view of an abduction positioning device 320 in accordance with embodiments of the disclosure. Abduction positioning device 320 includes an abduction wedge 322 or wedge frame that functions as a support member and carries the load of the patient's arm. Abduction wedge 322 may be constructed of an aluminum alloy base, over which EVA foam is molded along with an outer layer of laminated lycra or Velcro loop fabric. In such embodiments, the EVA and fabric may provide the abduction wedge a soft touch element to relieve pressure point and possible pain associated with wearing the orthosis. The overall size of the abduction wedge 322 is approximately 3 in. wide×6.85 in. tall×10.5 in. wide×0.375 in. thick.

Abduction positioning device 320 also includes a rotational insert 324 configured to engage with the abduction wedge 322 and house a rotational coupling member 326. In some embodiments, the rotational insert 324 is snapped into the abduction wedge 322 and serves to set the angle of the rotational coupling member 326 and in turn the patient's arm. The rotational insert 324 may be constructed from nylon and is approximately 1.75 in. outer diameter×0.85 in. tall×0.60 in. inner diameter. The rotational insert 324 may include two features which snap into the wedge frame to retain the rotational insert 324 and may include two keyed features to prevent rotation of the rotational insert 324 relative to the wedge frame. In some embodiments, rotational insert 324 also includes teeth which mate with the rotation coupling member 326 to hold the desired position, in fixed increments (such as 18° increments). The inner diameter of the rotational insert 324 may allow a locking member (such as a rod or skewer) to pass through so that the assembly may be locked into fixed position.

Figure 11:
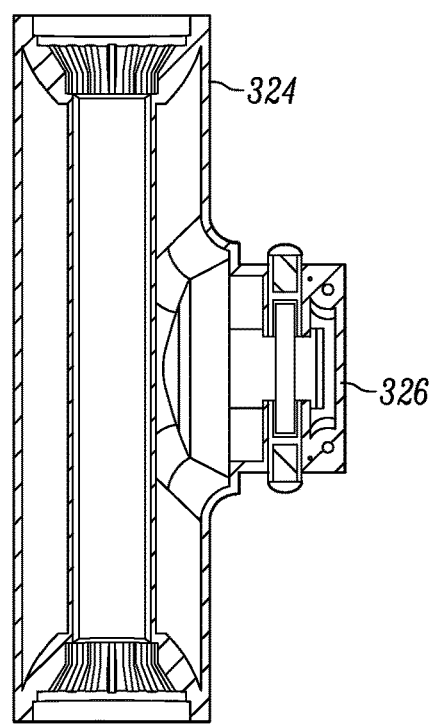
FIG. 11 illustrates a cross-sectional view of an external/internal rotation coupling member.

FIG. 11 illustrates a cross-sectional view of external/internal rotation coupling member or rotational coupling member 326. The rotational coupling member 326 may include six components—two halves of the rotational coupling member itself, two buttons, and two springs. Each coupling member may be constructed from nylon and is approximately 6.25 in. tall×1.75 in. diameter with an engagement member or cylindrical protrusion at the center which is approximately 2.25 in. diameter×1 in. tall. The rotational coupling member 326 may include teeth at either end which correspond to the teeth in the rotational insert 324, with increments at fixed positions. e.g. every 18°. The engagement member at the center may include openings for two spring loaded buttons and two rectangular features which matingly engage a coupling feature on the cradle device 330. FIG. 12 shows the two buttons and the two springs. The buttons may be constructed from nylon and are approximately 0.75 in.×0.925 in.×0.30 in. The springs may have dimensions of 0.156 in. diameter×1.25 in. overall length. In some embodiments, the two buttons reside in channels within the rotational coupling member 326 so as to only allow for a linear inward/outward motion. The two springs may be constrained to the two buttons via cylindrical pegs which extend into the inner diameter of the springs, again so as to only allow the two buttons to move in a linear fashion. The two halves of the rotational coupling member 326 are then fastened together, once assembled with the two buttons and two springs, via snap features and screws.

In some embodiments, a locking member or locking skewer (not shown) serves to rigidly lock the abduction positioning device 320 together and maintain the position of the rotational coupling member 326 relative to the abduction wedge 322. The locking skewer may be constructed from nylon and is approximately 7.15 in. tall with a major diameter of 2 in. culminating as a knob and a shaft diameter of 0.60 in. In some embodiments, the locking skewer is placed inside diameter of the rotational insert 324 and includes teeth and two keyed features which match that of the rotational insert 324. In some embodiments, there is also a 0.50 in. minor diameter internal female thread feature which mates with a male thread feature of the locking skewer. At one end of the locking skewer is a locking knob configured to allow for the user's fingers to grip the knob and rotate it into a closed or open position, locking or releasing the skewer.

Figure 12A:
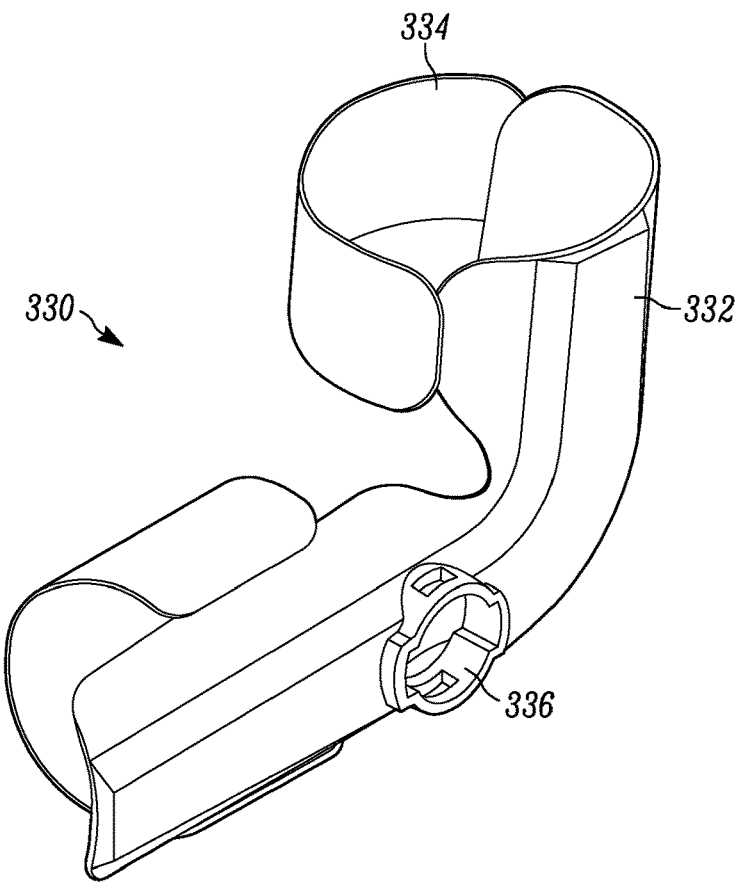
FIG. 12A illustrates an outer isometric view of an arm shell assembly.
Figure 12B:
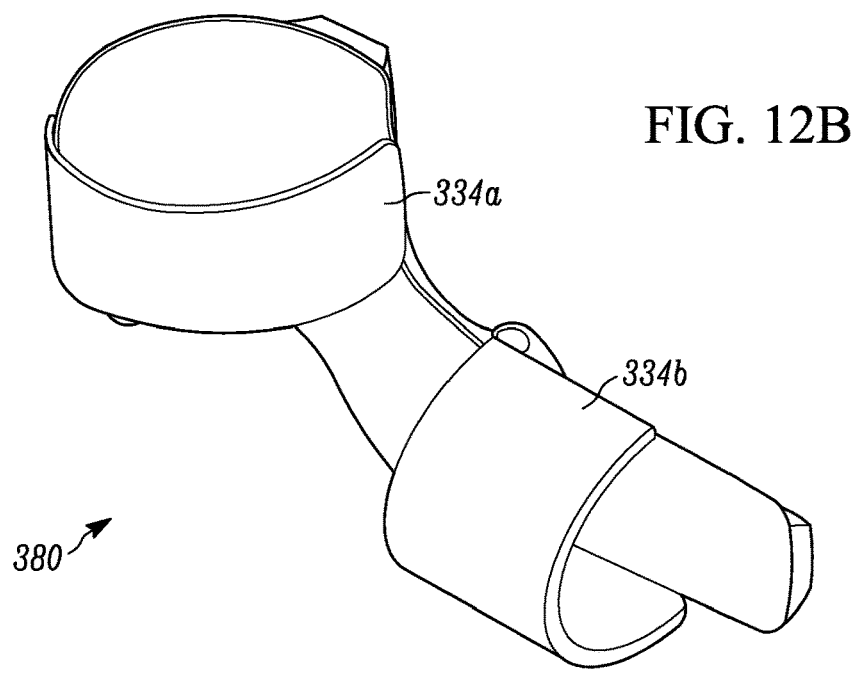
FIG. 12B illustrates an inner isometric view of an arm shell assembly.
Figure 13:
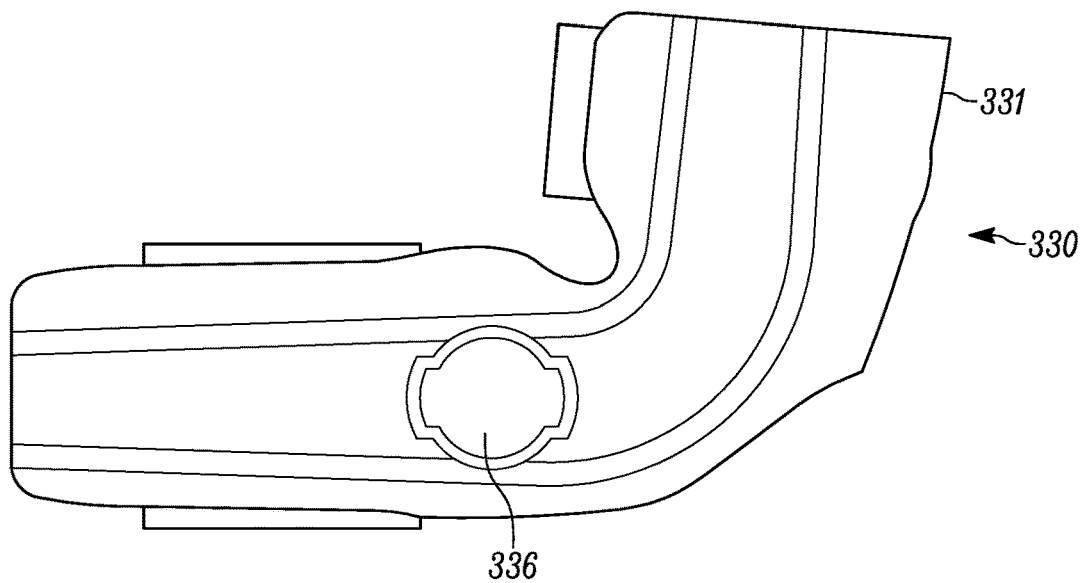
FIG. 13 illustrates an arm shell having a coupling feature.

FIGS. 12A and 12B illustrate different views of cradle device in accordance with embodiments of the disclosure. As shown, the cradle device 332 includes an arm shell 331. Arm shell 331 may be constructed from a combination of nylon and polypropylene and is approximately 13 in.×6.5 in.×5 in. Arm shell 331 interfaces with the rotational coupling member 326 via an attachment mechanism 336. In some embodiments, attachment mechanism 336 mates with the engagement member and two buttons on the rotational coupling member 326 to constrain the arm shell 331 to the abduction positioning device 320.

In some embodiments, arm shell 331 includes Velcro to allow fasteners 334 to attach and wrap around the arm of the patient. In some embodiments, a liner (not shown) attaches to the arm shell 331 on an interior surface and provides padding to the arm.

Fasteners 334 may include a biceps cuff 334a and a forearm cuff 334b. Biceps cuff 334a may attach to the arm shell 331 via Velcro and is meant to wrap around the patient's arm at the user's biceps. The biceps cuff 334a may be constructed from a combination of moisture wicking spacer fabric. Velcro hook/loop, edge banding material and molded strap tabs. The biceps cuff 334a is approximately 12 in.×4 in. when the pattern is laid flat. The Velcro attachment is meant to allow for adjustability to accommodate various size arm anatomy.

The forearm cuff 334b may attach to the arm shell 331 via Velcro and is meant to wrap around the patient's arm at the user's forearm. The forearm cuff 334b may be constructed from a combination of moisture wicking spacer fabric. Velcro hook/loop, edge banding material and molded strap tabs. The forearm cuff is approximately 10 in.×4 in. when the pattern is laid flat. The Velcro attachment is meant to allow for adjustability to accommodate various size arm anatomy.

In some embodiments, a forearm release or drop may be achieved by removing the forearm cuff 334b so that the forearm is free to move or by keeping the forearm strapped into the arm shell 331 and engaging a button (not shown) which unlocks a hinge at the elbow so that the forearm can flex and extend from 90 degrees (locked position) to 180 degrees (arm extended straight).

The liner or soft goods which line the arm shell 331 may be constructed from a combination of moisture wicking fabric laminated to breathable foam. The dimensions of the liner are such that they at least partially line the interior of the arm shell 331 when attached. The soft goods can be attached via plastic rivets or Velcro hook and loop.

In some embodiments, Velcro hook/loop is applied to the outside of the arm shell 331 in the areas where the biceps cuff 334a and forearm cuff 334b will attach. The soft goods which line the interior of the arm shell 331 are applied and held in place with plastic rivets which snap into corresponding holes in the shell body. The biceps cuff 334a and forearm cuff 334b are then attached to the Velcro on the outside of the arm shell 331.

Figure 14:
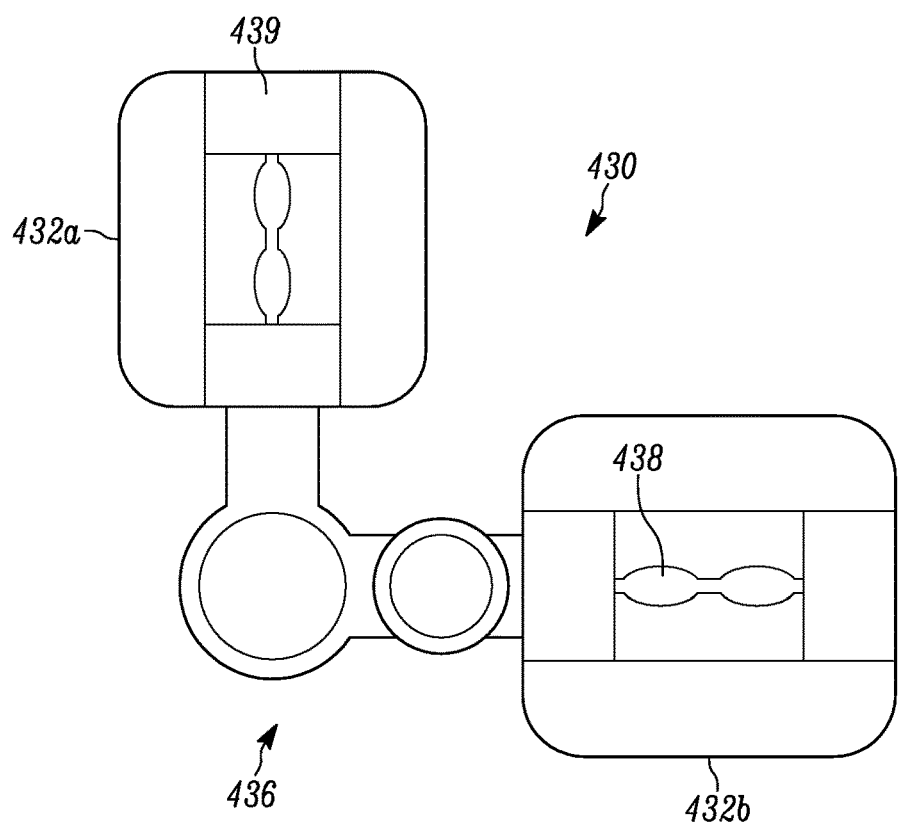
FIG. 14 illustrates an arm shell having two symmetric components.

FIG. 14 illustrates an arm shell having two symmetric components according to some embodiments of the disclosure. For example, arm shell 430 may include a biceps cradle or support 432a and a forearm cradle or support 432b. The length of the supports 432 may be extendable by sliding the end 439 of a support outward along a support bar 438. This essentially moves the end 439 of support 432 away from attachment mechanism or joint 436. As shown, there are two attachment mechanisms 436 for attachment with abduction positioning device 320.

Figure 15:
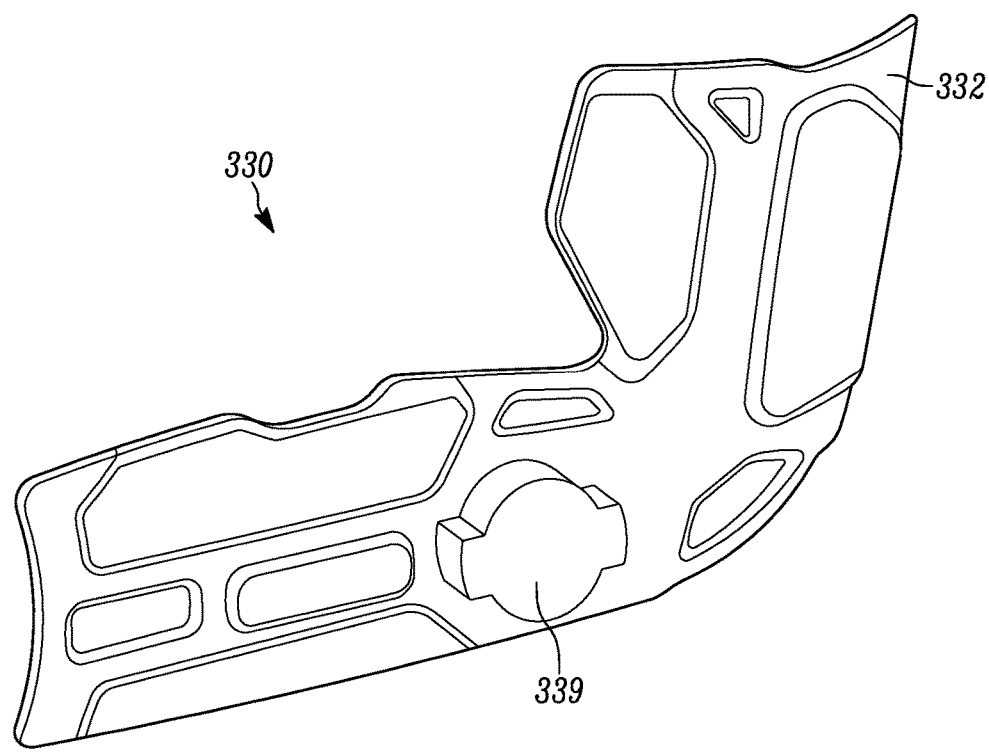
FIG. 15 illustrates a three dimensional view of an arm shell according to an embodiment of the disclosure.
Figure 16:
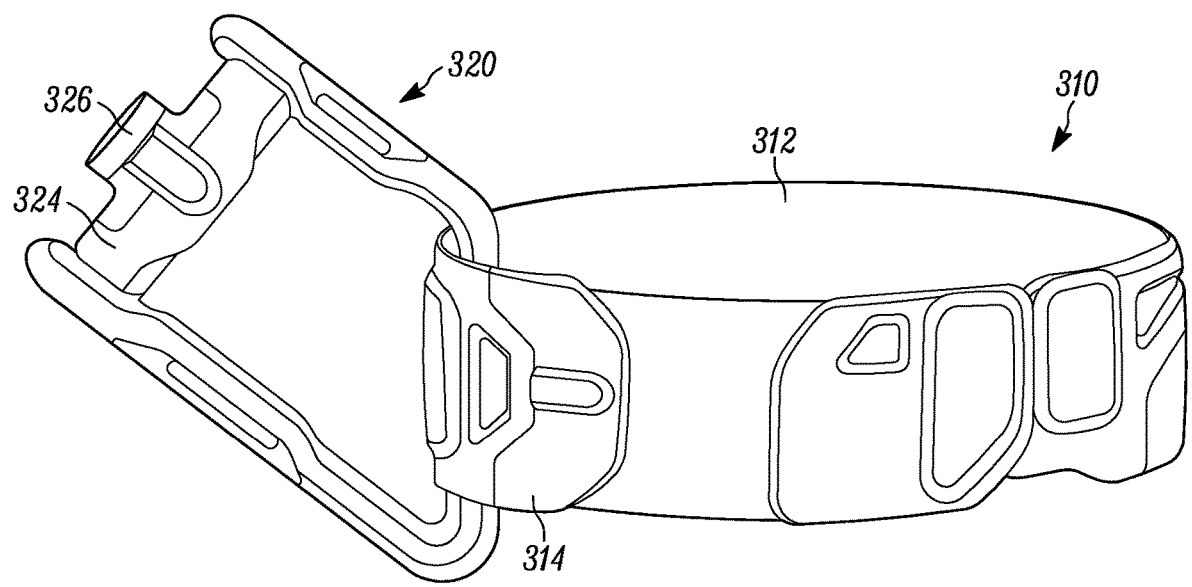
FIG. 16 illustrates a three dimensional view of a wedge assembly attached to a waist belt according to an embodiment of the disclosure.

FIG. 15 illustrates a three dimensional view of an arm shell according to an embodiment of the disclosure and FIG. 16 illustrates a three dimensional view of a wedge assembly attached to a waist belt according to an embodiment of the disclosure. Collectively. FIGS. 15 and 16 represent a complete assembly of a shoulder orthosis. To assemble the orthosis, the support device 310 is first pulled through an opening of the abduction positioning device 320 until the center panel lines up with the abduction wedge. The abduction wedge then nests into the contour of the support device 310 center panel. Finally the cradle device 330 is pressed onto the engagement member of the rotational coupling member of the abduction wedge via an attachment feature 339 of the cradle device 330. This causes the buttons on the rotation coupling member to depress via ramps molded into the attachment feature 339 of the cradle device 330 and then snap back out and into the body of the attachment feature 339 of the cradle device 330. The cradle device 330 is then securely affixed to the abduction positioning device 320.

When fitting the orthosis to a patient, a first step is to size the belt, as it is a universal fit. Remove the front outer and inner attachment panels from the belt and set aside; they are held to the soft goods via Velcro hook and loop. Align the center panel of the belt above the patient's iliac crest on the affected side of the body. Wrap the soft good portion of the belt facing forward around the patient's waist and trim to length; using scissors cut through the soft goods so that the front outer attachment panel will ultimately land at the patient's centerline. Wrap the soft good portion of the belt facing backwards around the patient's waist and trim to length; using scissors cut through the soft goods so that the front inner attachment panel will ultimately land at the patient's centerline. Reattach the front outer attachment panel to the short side of the soft goods of the waist belt which faces forwards. Reattach the front inner attachment panel to the long side of the soft goods of the waist belt which faces backwards and wraps behind the patient's waist. The waist belt should now be snuggly fit to the patient's waist; check to make sure the waist belt is not loose, re-cutting the soft goods if necessary. Now remove the waist belt from the patient for use after the next step.

Next select either the 45° or neutral abduction wedge frame depending upon the desired protocol. Now set the degree of external or internal rotation by aligning indication marks on the rotation coupling member to the corresponding degree marks on the wedge frame and seat the rotation coupling member over the rotational insert in the frame. The teeth of the rotation coupling member should now be engaged with the teeth of the rotational insert thus setting the amount of internal or external rotation desired. Slide the locking skewer through the keyed hole in the wedge frame and the hole in the rotation coupling member so that it protrudes from the bottom of the rotational insert of the wedge frame. Take care to align the keyed features of the locking skewer with those keyed features of the wedge frame. Now thread locking knob onto the locking skewer shaft protruding from the bottom of the wedge frame and turn clockwise until seated tightly. The external/internal rotation position of the abduction wedge is no set, along with the amount of abduction set by the frame selection (either 45° or neutral).

The abduction wedge can now be secured to the patient's body by sliding the short end of the waist belt through the center opening in the body of the abduction wedge. Center the abduction wedge in the contoured portion of the waist belt center panel such that the inner face of the abduction wedge opposite the rotation coupling member is coincident with the inside face of the center panel. With the abduction wedge now nested in the contour of the waist belt center panel place the assembly above the patient's iliac crest on the affected side of the body and wrap the long end of the waist belt soft goods behind the patient, bringing it around to the front. Now bringing the short end of the waist belt soft goods around the front of the patient, the front inner and outer attachment panels can now be connected via the Fidlock® snap fasteners or any suitable magnetic fastening or buckling interface. This will securely hold the abduction wedge in position relative to the patient's body.

Finally attach the arm shell to the arm on the affected side of the patient by seating the arm in the soft goods of the shell. Now, with the biceps cuff attached to the posterior side of the shell via Velcro hook and loop, bring the biceps cuff around the biceps and secure to the Velcro hook and loop on the anterior side of the shell. Repeat a similar process for the forearm cuff, with the forearm cuff attached to the distal side of the shell via Velcro hook and loop, bring the forearm cuff around the forearm and secure to the Velcro hook and loop on the superior side of the shell. Bring the arm shell to the abduction wedge and snap the coupling feature of the arm shell to the rotation coupling member. As the arm shell is slid over the mating feature of the rotation coupling member the spring loaded buttons on the rotation coupling member will engage with ramps on the coupling feature of the arm shell and depress. When the coupling feature of the arm shell is fully seated on the mating feature of the rotation coupling member the buttons return to their free height in corresponding holes in the arm shell thus locking the assembly together. The orthosis is now fit to the patient.

The shoulder orthosis described herein can be constructed from a number of alternative materials and has numerous uses and ranges. For example, for the waist belt attachment and center panels, the panels are constructed from low density (70 kg/m$^3$) and high density (80 kg/m$^3$) polyethylene foam sheet which is molded to shape. Alternatively, the panels can be injection molded from polypropylene and function in the same manner.

The soft goods can be constructed from polyethylene or EVA foam core molded to shape with loop mesh laminated to the outer surface and moisture wicking spacer fabric laminated to the inner surface. Alternatively, the soft goods of the waist belt can comprise moisture wicking spacer fabric trimmed in an edge banding material. Overall, the waist belt could vary in length from 18 in. to 65 in. to cover a range of body types and waist sizes.

For the abduction wedge, the wedge frame can be constructed from an aluminum substrate and over molded with EVA foam and laminated with a stretch fabric or UBL nylon. The wedge frame could also be over molded with different density foams, fabrics or textiles on either one or both sides. Alternatively the frame could be an injection molded part constructed from nylon. ABS or other suitably strong plastic resin. The current embodiment of the wedge frame comes in two configurations. 45° and neutral, but could also be adjustable within a range from neutral to 90° of abduction. Additionally, the wedge frame could be in a range of different thicknesses, widths or shapes based on strength requirements and geometry.

The rotation coupling member can be injection molded from nylon, but it could also be molded from ABS or other suitably strong plastic resin. Internal to the rotation coupling member are teeth which set the degree of rotation relative to the wedge frame. Currently these are set at 180 increments but could be within a range of 5° to 90° increments. The diameter around which the teeth are patterned is currently 1.30 in. but could range from 0.75 in. upwards depending on the strength requirements and size envelope of the surrounding components. The coupling mating feature with the arm shell can also range in size from 1 in. to 3 in. in diameter and 1 in. to 4 in. in length. The overall height of the rotation coupling member is 6.25 in. but can vary in a range from 1 in. to 8 in.

The locking skewer may be injection molded from nylon, but it could also be molded from ABS or other suitably strong plastic resin. The size and shape of the locking skewer can vary with that of the rotation coupling member, as they are mating components.

The locking knob may be injection molded from nylon, but it could also be molded from ABS or other suitably strong plastic resin. The size and shape of the locking knob can vary with that of the locking skewer, as they are mating components. The thread size and form can vary between the knob and skewer depending on the overall size and geometry of the components and the strength requirements. Additionally the connection can be something other than a threaded connection, such as: a snap feature with a release mechanism, a magnetic connection, a quarter turn fastener, or Christmas tree shaped barb. The finger grip to turn the knob can also vary in height, width and shape to give the best ergonomic shape which conforms with the anatomy of the user.

The rotational insert may be injection molded from nylon, but it could also be molded from ABS or other suitably strong plastic resin. The size and shape of the rotational insert can vary with that of the rotation coupling member, locking knob and locking skewer, as they are mating components.

The arm shell may be injection molded from a combination of nylon and polypropylene, but it could also be molded from ABS or other suitably strong plastic resin. The overall size and shape can vary to capture a range of arm size and anatomical shapes. A movable extension to support the hand and wrist may be included, such as shown in FIG. 14. The shell can also be a single or multiple component assembly utilizing a nylon or ABS backbone with a flexible polypropylene shell.

The biceps and forearm cuffs may be constructed from a moisture wicking spacer fabric with edge banding and Velcro hook and loop attachment to the shell. Alternatively the cuffs could be constructed from a moldable aluminum over molded or covered with formed foam and laminated fabric. The attachment to the arm shell can alternatively be a trimmable fabric or dual sided hook and loop material which is secured to the shell through a slot on one side and threaded through a slot on the other side, then folded back onto itself for closure. Additionally the cuffs could use molded buckles which snap onto or attach to the shell and utilize straps which would be adjustable. The size and shape of the cuffs can also vary to fit patient anatomy and arm size.

The soft goods which line the interior of the shell (e.g., form the liner) may be constructed from an open or closed cell foam laminated with a moisture wicking spacer fabric. The soft goods could utilize alternative foams and laminates, such as memory shape foams and fabrics which regulate temperature as well as moisture.

Figure 17:
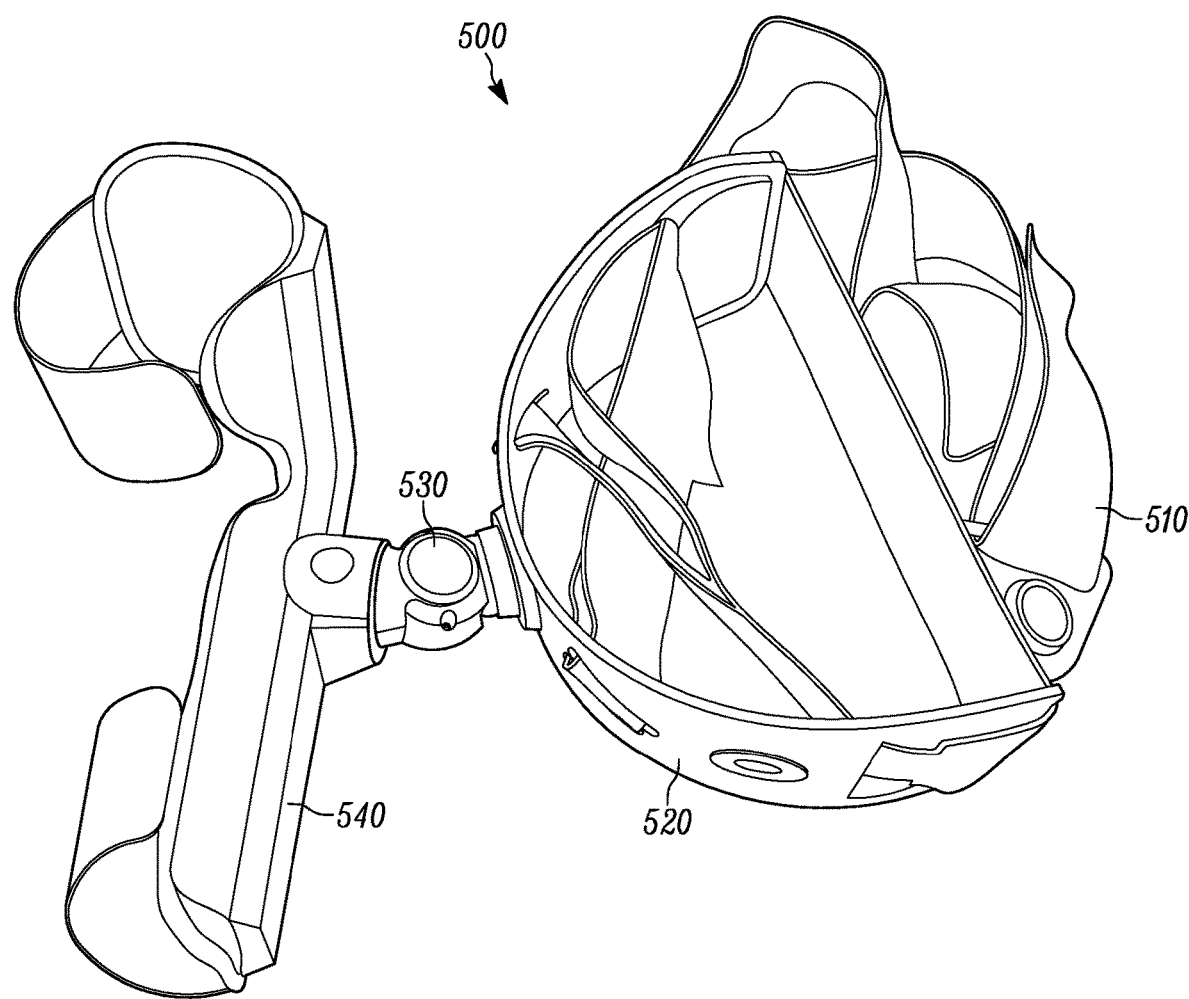
FIG. 17 illustrates a shoulder brace according to an embodiment of the disclosure.

FIG. 17 illustrates a shoulder brace 500 according to an embodiment of the disclosure. Shoulder brace 500 is configured to immobilize the arm, and in turn the shoulder joint, in neutral abduction/adduction to 45°, external rotation of 0-50° and internal rotation of 0-60°. Shoulder brace 500 includes three primary components: a support device 510, an abduction positioning device 520 and a cradle device 540, which allow for a low profile design while minimizing the need for additional straps which go around the neck. The abduction positioning device 520 may include an external/internal rotation coupling member or rotational coupling member 530. In some embodiments, cradle device 540 provides a drop out means to allow for flexion/extension of the forearm which facilitates daily living activities.

Figure 18:
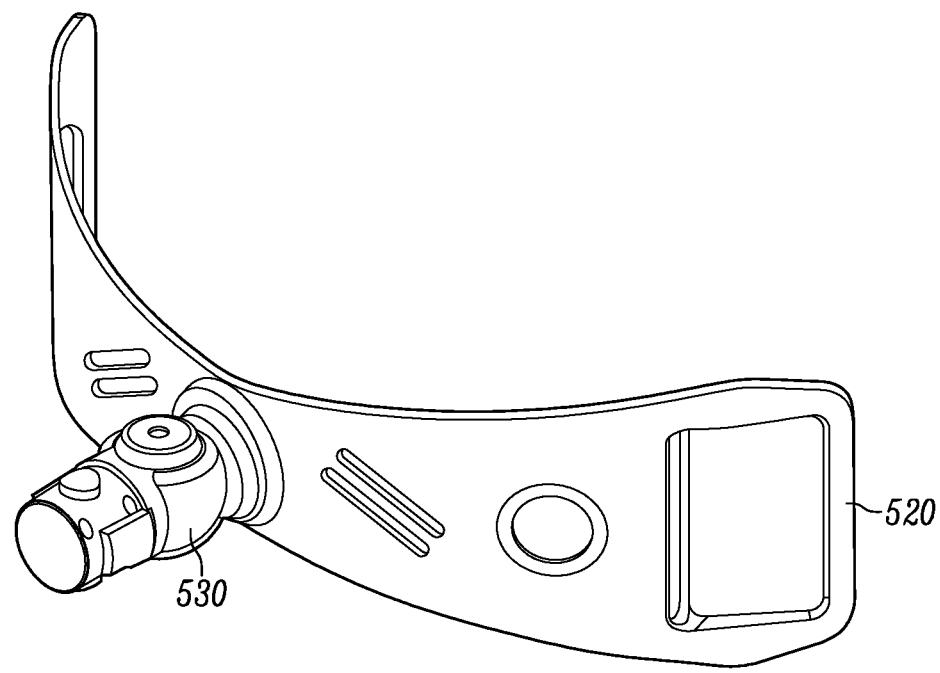
FIG. 18 illustrates an abduction arch connected to an external/internal rotation coupling member.

FIG. 18 illustrates a support device or arch 520 configured to conform to the user's torso in communication with external/internal rotation coupling member 540. In some embodiments, the arch 520 provides the means by which abduction of the user's arm is adjusted. For example, arch 520 may be a flexible member constructed from polypropylene that can conform to different size users or patients and adjust abduction by changing curvature. This change in curvature of the arch 520 may be accomplished by lengthening or shortening a strap (not shown) that runs along the base of the arch 520. This strap length change moves the apex of arch 520 (where cradle device 540 attaches) further out or closer into the torso, thereby increasing or decreasing the abduction of the user's arm. In some embodiments, arch 520 is approximately 6 in. tall×24 in. long (arc length)×19 in. across base×0.25 in. thick.

Figure 19:
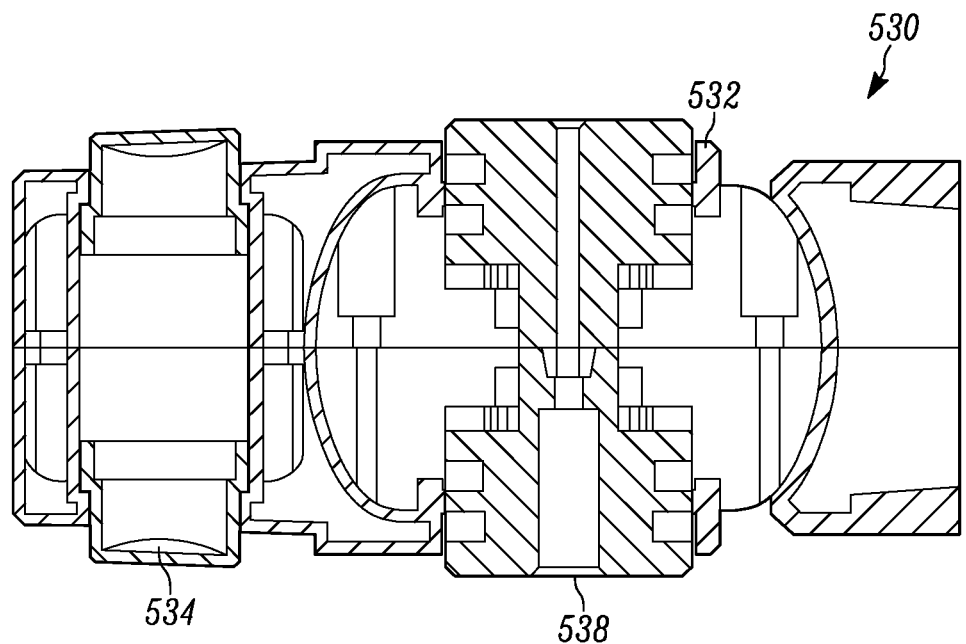
FIG. 19 illustrates a cross-sectional view of the external/internal rotation coupling member of FIG. 18.

FIG. 19 illustrates a cross-sectional view of external/internal rotation coupling member 530. In some embodiments, external/internal rotation coupling member 530 sets the rotation of the arm relative to the body by means of teeth 532 within an outer rotation coupling, an inner rotation coupling and a rotation button 538. FIG. 5 shows the cross section of the assembly. In some embodiments, the outer rotation coupling mates with the inner rotation coupling and is where the cradle device 540 attaches. External rotation coupling is generally cylindrical in shape with a minor diameter approximately of 1.75 in×1.5 in. long. Protruding from the cylindrical body is another cylindrical body perpendicular to it with teeth patterned around the interior. These parts may be constructed from either a nylon or ABS polymer.

In some embodiments, the inner rotation coupling mates with the outer rotation coupling. Inner rotation coupling is generally spherical in shape with flat ends and a diameter of approximately 2.5 in. It has matching teeth which overlap the outer rotation coupling when viewed from the top. There is an approximately 0.25 in. wide slot in the back of the body to allow the coupling to pivot in the sagittal plan of the body (e.g., when user is wearing device 500). These parts may be constructed from either a nylon or ABS polymer.

In some embodiments, rotation button 538 has teeth that are patterned around its circumference which when mated within the teeth 532 of the outer and inner couplings, lock the two couplings relative to each other. The button diameter is approximately 1.23 in. and is approximately 1.125 in. in length. There are two grooves cutting through the teeth circumferentially which are approximately 0.150 in. wide, allowing of the teeth of the outer rotation coupling to pass through. This part may be constructed from either a nylon or ABS polymer.

Arm buttons 534 may be constructed from nylon and are approximately 0.75 in. diameter×0.625 in. tall. A spring may be nested inside the diameter of the buttons 534 so that they can retract and return when the cradle device 540 is attached. The two buttons 534 reside in channels within the outer rotation coupling member so as to only allow for a linear inward/outward motion. This part may be constructed from either a nylon or ABS polymer. Two springs (not shown) reside under the rotation button 538 and within the inner rotation coupling. The springs are approximately 0.70 in. diameter×0.5 in. tall and made from spring steel.

Figure 20:
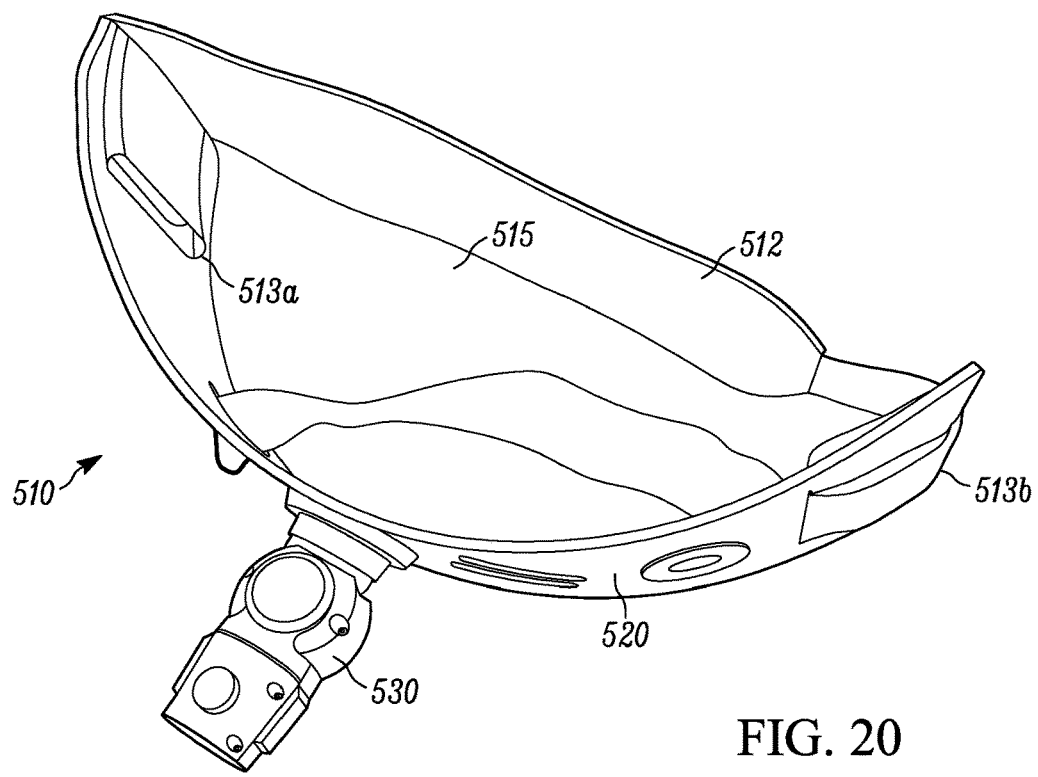
FIG. 20 illustrates an inner strap configuration of a support device.
Figure 21:
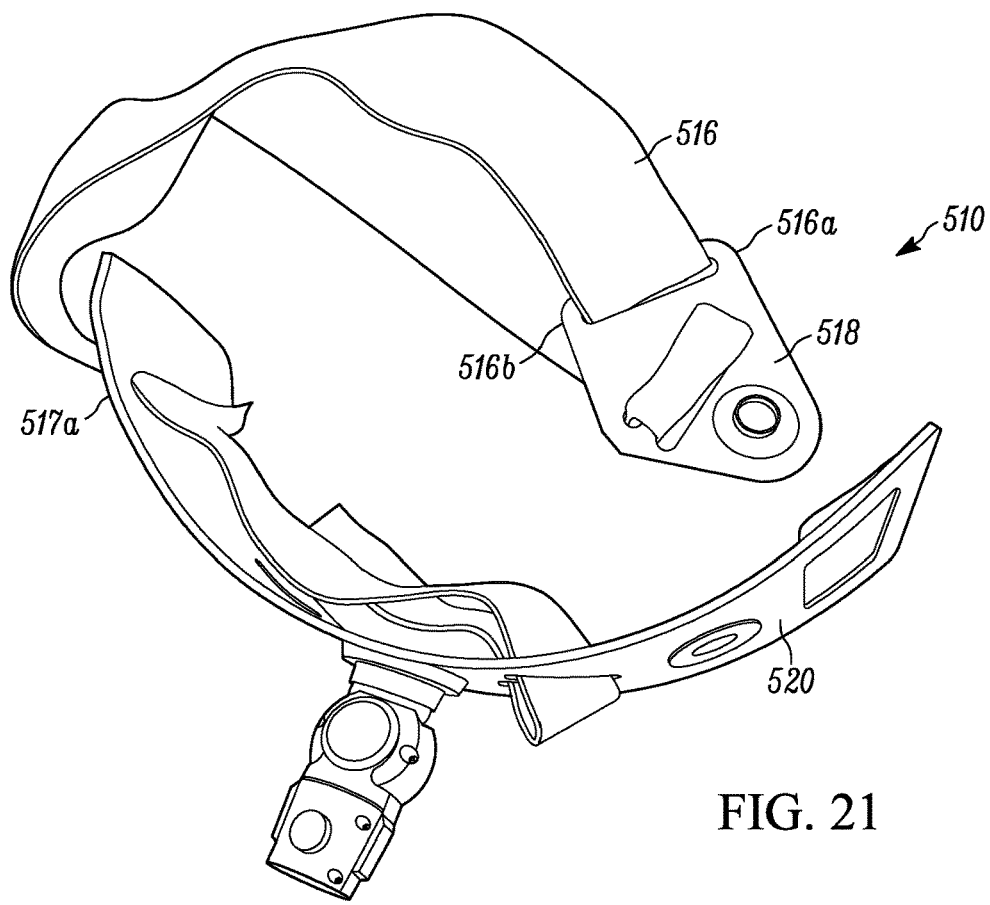
FIG. 21 illustrates an outer strap configuration of a support device.

FIG. 20 illustrates an inner strap configuration of support device 510 and FIG. 21 illustrates an outer strap configuration of a support device 510. The inner strap configuration includes inner strap 512, which has a generally straight linear geometry and is approximately 4 in. wide, which then necks down to 2 in. wide to pass through slots 513a and 513b in arch 520. In some embodiments, inner strap 512 is configured to form a partial barrier 515 between the torso of the user and abduction positioning device 520.

The outer strap configuration includes an outer strap 516. The outer strap 516 may be a "Y"-shaped belt having a first portion with one end and a second portion with two ends 516a and 516b. The Y-shaped belt may be approximately 4 in. wide on two ends 516a, 516b and then necks down to 2 in. wide to pass through slots 517a in arch 520. In some embodiments, two ends 516a, 516b of the outer strap 516 then connect to a semi-rigid panel 518 which houses a fastener, such as a Fidlock® fastener or any suitable magnetic fastening or buckling interface.

Figure 22:
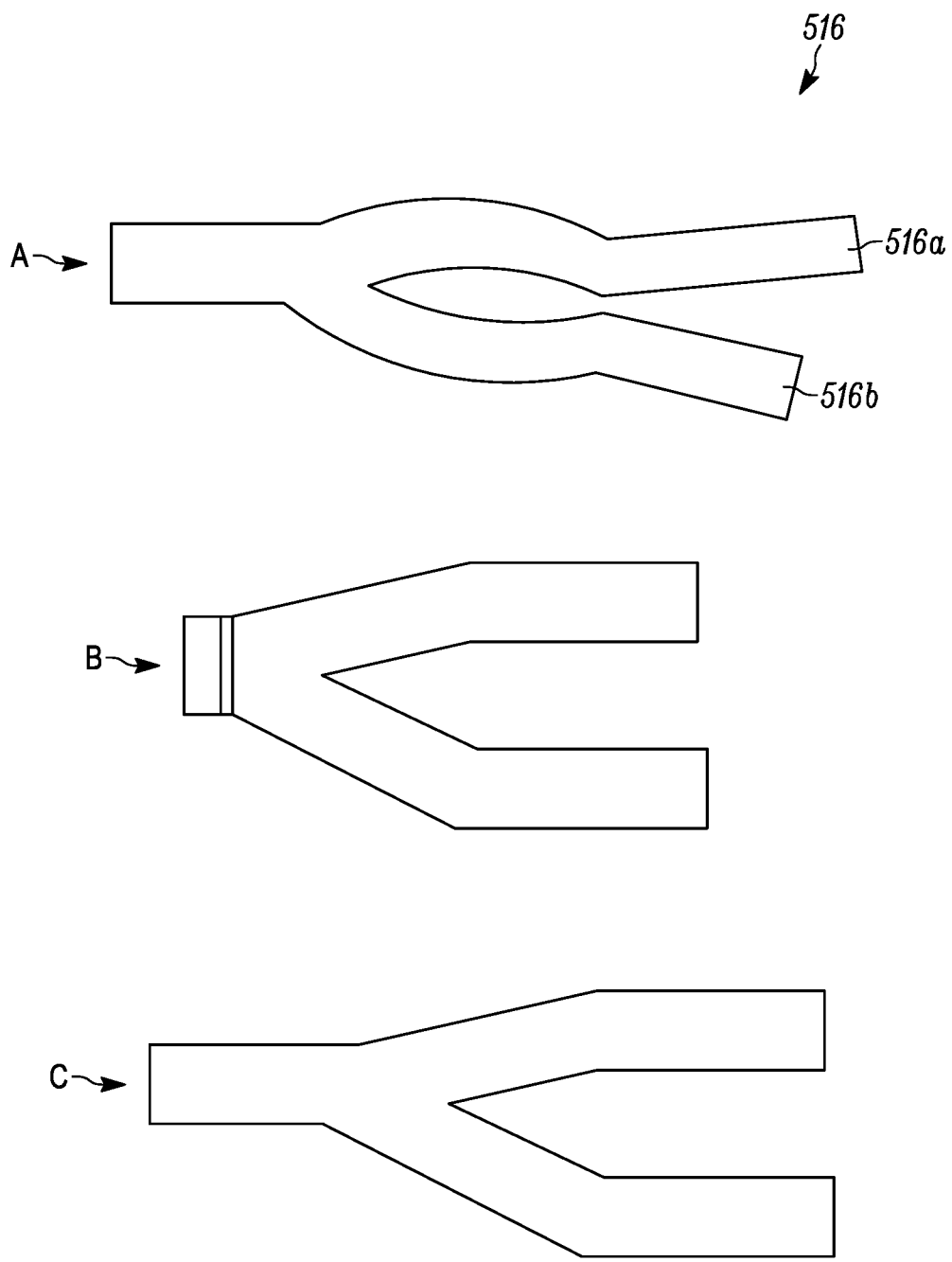
FIG. 22 illustrates a plurality of y-shaped strap outer strap designs.
Figure 23:
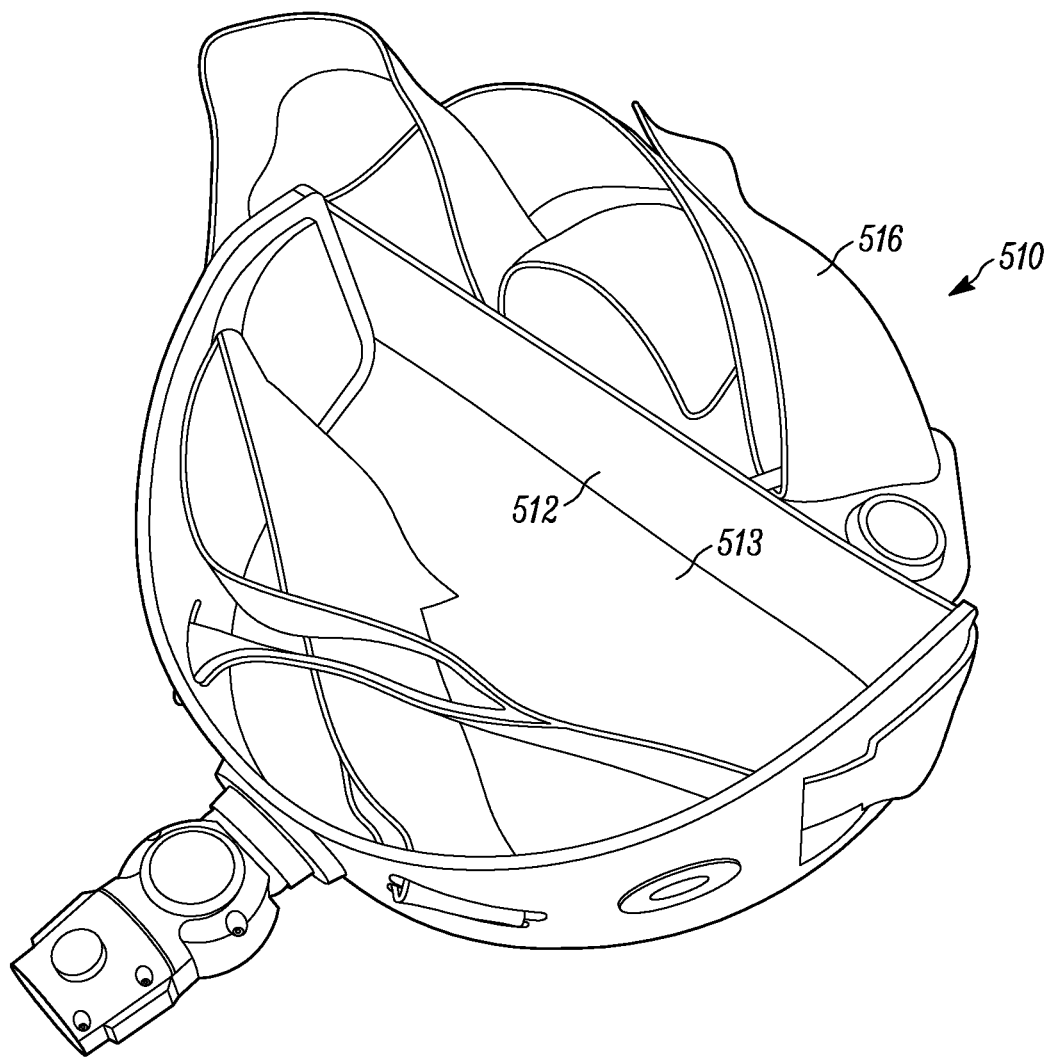
FIG. 23 illustrates an assembled support device.

FIG. 22 illustrates a plurality of y-shaped outer strap designs A, B, and C and FIG. 23 illustrates an assembled support device 510. In some embodiments, inner straps 512 and outer strap 516 are constructed from moisture wicking spacer fabric on one side and unbroken loop (UBL) nylon fabric on another side.

Figure 24:
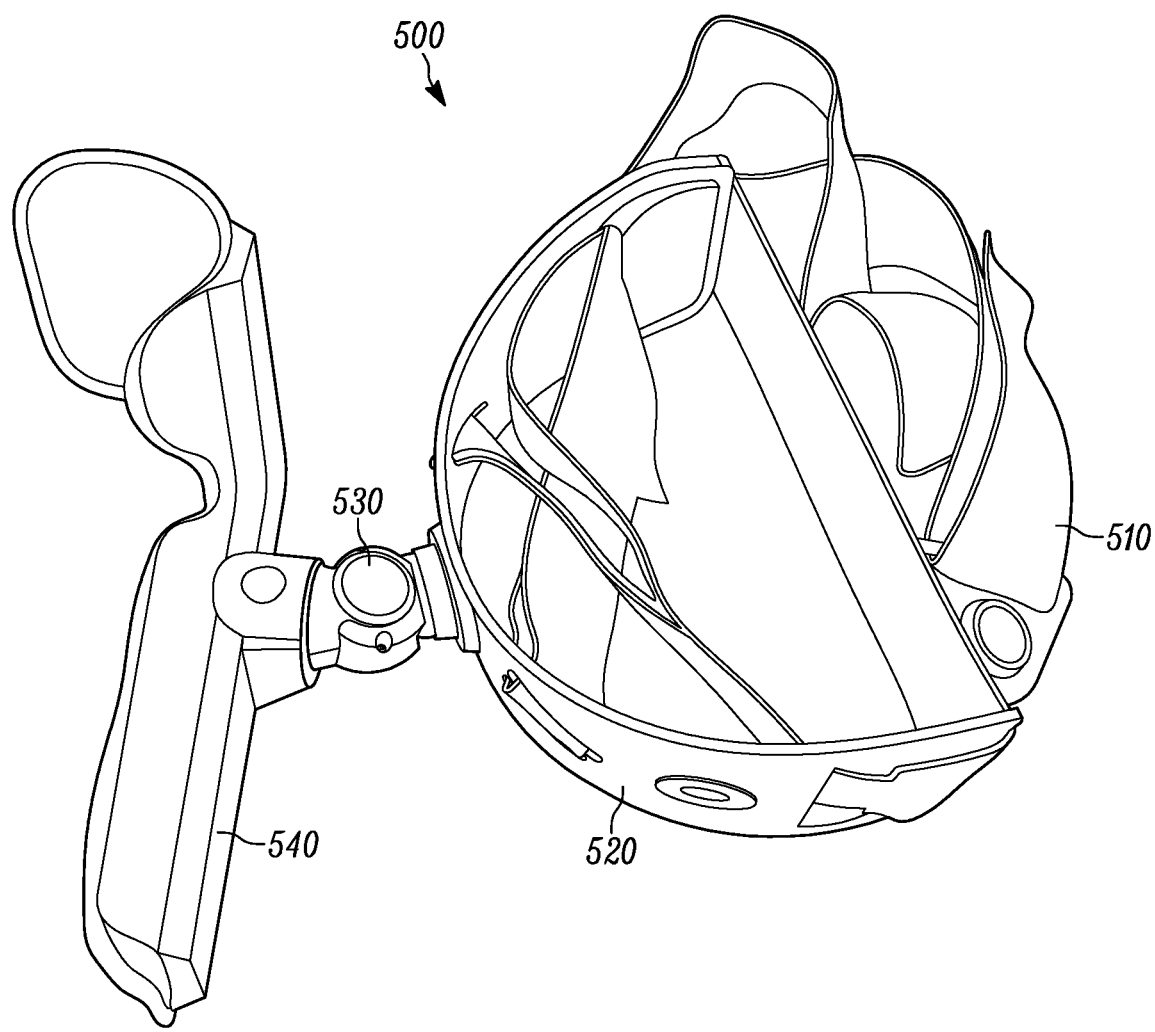
FIG. 24 illustrates an assembled shoulder brace according to an embodiment of the disclosure.

FIG. 24 illustrates an assembled shoulder brace 500 according to an embodiment of the disclosure. While not specifically depicted in a separate figure because a similar cradle device is described in FIG. 12, cradle device 540 includes an arm shell configured to interface with the rotation coupling member 530. The arm shell may be constructed from a combination of nylon and polypropylene and is approximately 13 in.×6.5 in.×5 in. The arm shell may include an attachment feature which mates with an engagement member and two buttons on the rotation coupling member 530 to constrain the arm shell to the abduction positioning device 520. In some embodiments, there is Velcro on the arm shell to allow a biceps cuff and forearm cuff to attach and wrap around the arm of the user. Finally, there may be soft goods which also attach to the arm shell to pad the arm.

In some embodiments, the external/internal rotation member 530 is attached to the arch 520 by a slot on the backside of the inner rotation coupling (e.g., when the two halves of the coupling are fastened). There may be protrusions in the arch 520 which mate to this slot and constrain the assembly to only pivot in the sagittal plane (when the patient is wearing device 500). The two halves of the outer rotation coupling are then seated in the inner rotation coupling halves such that the teeth 532 of each overlap. The arm buttons 538 and spring are seated within the halves of the outer rotation couplings and then the halves are fastened. The two 0.70 in.×0.50 in. springs are placed in either side of the inner rotation coupling and the rotation buttons 538 are then inserted into the inner coupling. The two rotation buttons 538 have a mating feature which orients and fixates one side of the button to the other such that the teeth of each align. A screw is then used to fasten the two buttons together. Now when the rotation button 538 is depressed from either side the circumferential groove in the button teeth will allow the teeth of the outer rotation coupling to pass so as to adjust the amount of external or internal rotation. A Fidlock® fastener or any suitable magnetic fastening or buckling interface may be attached to a circular boss on the arch 520 to allow for attachment of the straps 510.

In some embodiments, there are two straps 512, 516 for the arch assembly. The inner strap 512 attaches to a slot 513b to the left of the external/internal rotation member 530 and then passes through a slot 513a on the right side opposite where it attaches. The strap 512 is then brought back around to the slot 513b on the left side and attached via hook and loop. This strap 512 adjusts the amount of curvature of the arch 520 by lengthening or shortening the strap 512 and in effect the amount of abduction of the user's arm. The outer strap 516 attaches to a slot 517a on the right of the external/internal rotation member 530 and then passes through an opposite slot opening on the left side (not shown). The outer strap 516 is in the shape of a "Y" such that the two ends 516a, 516b of the strap 516 connect to a semi-rigid panel 518 which houses a Fidlock® fastener or any suitable magnetic fastening or buckling interface. This "Y" shape may allow the orthosis to fit a multitude of body types and prevent the orthosis from sliding down the user's torso. The panel 518 can then attach to a corresponding fastener on arch 520. This facilitates one handed application of the orthosis.

In some embodiments, a Velcro hook/loop is applied to the outside of the arm shell in the areas where the biceps and forearm cuff will attach. The soft goods which line the interior of the shell are applied and held in place with plastic rivets which snap into corresponding holes in the shell body. The biceps and forearm cuffs are then attached to the Velcro on the outside of the shell.

When fitting the orthosis to a patient, a first step is to size the inner strap to obtain the correct amount of abduction required for the patient. The strap end is pulled tight and cut to length. An alligator tab is then attached to the end of the strap via hook and loop and secured in place. This has now tensioned the arch and adjusted the curvature to provide a set amount of abduction when the orthosis is placed against the user or patient's body. Next the outer strap is adjusted such that the 4 in. wide portion of the strap is in the outer most slot towards the posterior of the patient. The fastening panel is then brought around the back of the patient, towards the front end attached to the Fidlock® fastener on the front of the arch. The two lengths of the "Y" of the outer strap are then adjusted so that the orthosis is snug on the patient's body. The excess of these straps can be cut and discarded. At this point, if the patient needs to put on or take off the orthosis, they only need to use the Fidlock® fastener or any suitable magnetic fastening or buckling interface.

The arm shell is next attached to the arm on the affected side of the patient by seating the arm in the soft goods of the shell. Now, with the biceps cuff attached to the posterior side of the shell via Velcro hook and loop, bring the biceps cuff around the biceps and secure to the Velcro hook and loop on the anterior side of the shell. Repeat a similar process for the forearm cuff, with the forearm cuff attached to the distal side of the shell via Velcro hook and loop, bring the forearm cuff around the forearm and secure to the Velcro hook and loop on the superior side of the shell. Bring the arm shell to the external/internal rotation member and snap the coupling feature of the arm shell to the outer rotation coupling. As the arm shell is slid over the mating feature of the rotation coupling, the spring loaded buttons on the rotation coupling will engage with ramps on the coupling feature of the arm shell and depress. When the coupling feature of the arm shell is fully seated on the mating feature of the rotation coupling, the buttons return to their free height in corresponding holes in the arm shell thus locking the assembly together. Finally, depress the rotation button to adjust the amount of external or internal rotation of the patient's arm. Release the button to allow the internal springs to equalize the button position and engage the teeth on the inner and outer couplings. The arm should now be locked into place and the orthosis fit to the patient.

In some embodiments, the arch structure may be constructed from polypropylene, polyethylene or another thermoplastic resin that allows for compliance so that the arch and change curvature without fatiguing or cracking. In some embodiments, the external/internal rotation member may be constructed from a number of thermoplastic resins, including nylon, nylon with glass fill, or ABS.

In some embodiments, the arm shell is injection molded from a combination of nylon and polypropylene, but it could also be molded from ABS or other suitably strong plastic resin. The overall size and shape can vary to capture a range of arm size and anatomical shapes. The addition of a movable extension to support the hand and wrist is also an option. The arm shell may be a single or multiple component assembly utilizing a nylon or ABS backbone with a flexible polypropylene shell. Additionally, the arm shell may be of a configuration such as the X-Act Rom Elbow product which utilizes a stamped metal frame (e.g., aluminum) and moldable cuffs.

In some embodiments, the biceps and forearm cuffs are constructed from a moisture wicking spacer fabric with edge banding and Velcro hook and loop attachment to the arm shell. Alternatively the cuffs may be constructed from a moldable aluminum over molded or covered with formed foam and laminated fabric. The attachment to the arm shell can alternatively be a trimmable fabric or dual sided hook and loop material which is secured to the shell through a slot on one side and threaded through a slot on the other side, then folded back onto itself for closure. Additionally the cuffs could use molded buckles which snap onto or attach to the shell and utilize straps which would be adjustable. The size and shape of the cuffs can also vary to fit patient anatomy and arm size.

In some embodiments, the soft goods which line the interior of the arm shell (e.g., the liner) are constructed from open or closed cell foam laminated with moisture wicking spacer fabric. The soft goods may utilize alternative foams and laminates, such as memory shape foams and fabrics which regulate temperature as well as moisture.

The disclosed shoulder orthosis has significant advantages over previous shoulder braces. Some of the advantages include its lightweight construction, ease of application with minimum steps, quick connect fasteners, as well as easy and quick abduction and external/internal rotation. Additionally, the brace provides a precise amount of abduction and external/internal rotation. Advantageously, the brace is breathable and includes a drop out design.

By separating the orthosis into three components the operating room staff is able to slide the waist belt under the patient without the extra bulk of the abduction mechanism and arm shell, unlike other products that combine all the components into one piece. Since the patient is unconscious or sedated having a separate waist belt component which is low profile makes it easier to position the product between the patient and the operating table. There are a minimum number of steps involved in applying the orthosis making it quick and easy for the operating room staff to apply. By using quick connect fasteners on the waist belt and a quick connect coupling between the abduction wedge and arm shell, applying the orthosis is quick and easy.

Using moisture wicking spacer fabric laminated to perforated foam the orthosis is breathable and manages heat at the point of application. The perforated foam and low profile design on the waist belt also improve the comfort of the orthosis, minimizing the amount of material around the patient's back. This has the added benefit of reducing the discomfort when the wearer of the orthosis is in a sitting or sleeping position by removing unnecessary bulk.

Many of the current products on the market do not allow for quick and easy adjustment of the abduction or external/internal rotation of the orthosis. By utilizing a locking skewer and knob design, external/internal rotation of the orthosis is quickly set to a precise amount. The use of inserts which have teeth spaced at desired increments it is possible to precisely set the amount of external/internal rotation and maintain that degree of rotation if the orthosis is taken off and put back on.

Additional features include the ability to drop the forearm out of the arm shell so that patients can function in daily life activities while still keeping the shoulder immobilized.

Methods of using the disclosed shoulder brace are likewise provided. Uses can include the treatment of glenohumeral dislocation or subluxation, capsular shifts, posterior shoulder stabilizations, Bankart repairs, release severe anterior capsule contracture, soft tissue strains or repairs, rotator cuff repairs, total shoulder replacement, superior labral repairs (SLAP), shoulder debridement, fractures (humerus, elbow, forearm), biceps tendon repair, elbow ligament/tendon repair, anterior shoulder laxation and AC joint reconstruction.

In some embodiments, the brace may be modified to include a spring loaded push button to lock and release the rotation coupling member via internal gear teeth.

Reference throughout this disclosure to "an embodiment" or "the embodiment" means that a particular feature, structure or characteristic described in connection with that embodiment is included in at least one embodiment. Thus, the quoted phrases, or variations thereof, as recited throughout this disclosure are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. An orthopedic shoulder device comprising:
   a cradle device configured to receive and support a portion of an arm of a user;

an abduction positioning device comprising:
  a flexible arch having an apex, and
  a rotation coupling member coupling the cradle device to the apex of the arch such that adjusting an amount of curvature of the flexible arch adjusts an angle of abduction of the arm of the user relative to a torso of the user; and
at least one strap coupled between at least two locations on the flexible arch such that the amount of curvature of the flexible arch is adjusted by adjusting an amount of the at least one strap coupled between the at least two locations on the flexible arch.

2. The shoulder device of claim 1, wherein the cradle device comprises:
an arm shell configured to provide a resting support for the arm of the user; and
a plurality of fasteners configured to surround and hold the arm of the user in place against the arm shell.

3. The shoulder device of claim 2, wherein the arm shell comprises a semi-rigid structure configured to restrict movement of the arm of the user.

4. The shoulder device of claim 2, wherein the arm shell further comprises a liner that covers a portion of an interior surface of the cradle and provides padding to the arm of the user.

5. The shoulder device of claim 1, wherein the at least one strap comprises an inner strap and the at least two locations on the flexible arch comprise:
a first slot located at a first portion of the flexible arch that is disposed in a first direction from the apex of the flexible arch; and
a second slot located at a second portion of the flexible arch that is disposed in a second direction from the apex of the flexible arch opposite the first direction.

6. The shoulder device of claim 5, wherein the inner strap is configured to form a partial barrier between the torso of the user and the flexible arch, the size of the partial barrier being adjustable by shortening or lengthening the inner strap.

7. The shoulder device of claim 1, wherein the at least one strap comprises an outer strap and the at least two locations on the flexible arch comprise:
a first slot located at a first portion of the flexible arch that is disposed in a first direction from the apex of the flexible arch; and
a fastener located at a second portion of the flexible arch that is disposed in a second direction from the apex of the flexible arch opposite the first direction.

8. The shoulder device of claim 7, wherein the outer strap is substantially Y-shaped, having a first end, a second end and a third end, and wherein the first end couples to the first slot and the second end and the third end couple to a semi-rigid panel configured to attach to the fastener.

9. The shoulder device of claim 7, wherein the outer strap is configured to be wrapped around the torso of the user.

10. The shoulder device of claim 1, wherein adjusting the amount of curvature of the flexible arch simultaneously adjusts a distance of the apex of the flexible arch from the torso of the user, thereby adjusting the angle of abduction of the arm of the user.

11. The shoulder device of claim 1, wherein at least a portion of the flexible arch is configured to conform to the torso of the user.

12. The shoulder device of claim 1, wherein the rotation coupling member comprises:
an outer rotation coupling;
an inner rotation coupling; and
a rotation button configured to:
  fix a relative orientation of the outer rotation coupling with respect to the inner rotation coupling in a first position, and
  allow relative rotation between the outer rotation coupling and the inner rotation coupling in a second position.

13. The shoulder device of claim 12, wherein the rotation coupling member is configured to adjust at least one of an angle of internal rotation and an angle of external rotation of the arm of the user relative to the torso of the user by adjusting a relative orientation of the outer rotation coupling with respect to the inner rotation coupling.

14. The shoulder device of claim 12, wherein the internal rotation coupling is matingly engaged with the external rotation coupling to form the rotation coupling member.

15. The shoulder device of claim 12, wherein the rotation button comprises a first plurality of teeth configured to mate with a second plurality of teeth of the outer rotation coupling when the rotation button is disposed in the first position.

16. The shoulder device of claim 15, wherein the rotation button comprises at least one groove cutting through the first plurality of teeth such that the second plurality of teeth of the outer rotation coupling rotate freely within the at least one groove when the rotation button is in the second position, thereby allowing adjustment of at least one of an angle of internal rotation and an angle of external rotation of the arm of the user relative to the torso of the user.

17. The shoulder device of claim 12, wherein the rotation coupling member further comprises:
an engagement member configured to couple the rotation coupling member to the cradle device; and
a plurality of engagement buttons configured to releasably engage the engagement member with the cradle device.

18. A rigid device for immobilizing a shoulder, comprising:
a cradle device configured to receive and support a portion of an arm of a user;
an abduction positioning device configured to immobilize an arm of the user in neutral abduction/adduction to about 45 degrees, external rotation of between about 0-50 degrees, and internal rotation of between about 0-60 degrees, the abduction positioning device comprising:
  a flexible arch having an apex, and
  a rotation coupling member coupling the cradle device to the apex of the arch such that adjusting an amount of curvature of the flexible arch adjusts an angle of abduction of the arm of the user relative to a torso of the user; and
a low profile support device comprising a waist strap and a shoulder strap configured to be wearable by the user and detachably secured to the abduction positioning device in a predetermined position.

19. The shoulder device of claim 18, wherein adjusting the amount of curvature of the flexible arch simultaneously adjusts a distance of the apex of the flexible arch from the torso of the user, thereby adjusting the angle of abduction of the arm of the user.

20. The shoulder device of claim 18, wherein the rotation coupling member comprises:
an outer rotation coupling;
an inner rotation coupling; and
a rotation button configured to:
  fix a relative orientation of the outer rotation coupling with respect to the inner rotation coupling in a first position, and allow relative rotation between the outer rotation coupling and the inner rotation coupling in a second position.

\* \* \* \* \*